US006794148B2

(12) United States Patent
Jindal et al.

(10) Patent No.: US 6,794,148 B2
(45) Date of Patent: Sep. 21, 2004

(54) HIGH SPEED, AUTOMATED, CONTINUOUS FLOW, MULTI-DIMENSIONAL MOLECULAR SELECTION AND ANALYSIS

(75) Inventors: Satish Jindal, Milton, MA (US); Fred Regnier, West Lafayette, ID (US); Kevin Williams, Natick, MA (US); Noubar Afeyan, Lexington, MA (US); Sandeep Paliwal, Mountain View, CA (US); David Evans, Natick, MA (US); Aruna Pingali, Westboro, MA (US)

(73) Assignee: PerSeptive Biosystems, Inc., Framingham, MA (US)

( * ) Notice: Subject to any disclaimer, the term of this patent is extended or adjusted under 35 U.S.C. 154(b) by 348 days.

(21) Appl. No.: 10/006,630

(22) Filed: Dec. 5, 2001

(65) Prior Publication Data
US 2002/0150926 A1 Oct. 17, 2002

Related U.S. Application Data

(62) Division of application No. 09/267,993, filed on Mar. 12, 1999, now Pat. No. 6,358,692, which is a continuation of application No. 08/670,670, filed on Jun. 26, 1996, now abandoned.
(60) Provisional application No. 60/000,518, filed on Jun. 26, 1995.

(51) Int. Cl.[7] ............... G01N 33/50; G01N 33/543
(52) U.S. Cl. .......... 435/7.1; 436/161; 436/518; 436/528; 530/413
(58) Field of Search ............ 435/7.1; 436/161, 436/518, 528; 530/413

(56) References Cited

U.S. PATENT DOCUMENTS

| 4,205,058 | A | 5/1980 | Wagner et al. ............. 424/1 |
| 4,705,616 | A | 11/1987 | Andresen et al. ......... 204/299 |
| 4,762,617 | A | 8/1988 | Stevens ..................... 510/635 |
| 4,879,247 | A | 11/1989 | Ohlson ...................... 436/527 |
| 4,883,958 | A | 11/1989 | Vestal ........................ 250/288 |
| 4,895,809 | A | 1/1990 | Schalbach et al. ......... 436/518 |
| 4,902,891 | A | 2/1990 | Vestal ........................ 250/281 |
| 4,937,200 | A | 6/1990 | Kumazawa et al. ....... 436/518 |
| 4,999,493 | A | 3/1991 | Allen et al. ................ 250/288 |
| 5,003,059 | A | 3/1991 | Brennan .................... 536/27 |
| 5,010,175 | A | 4/1991 | Rutter et al. ............... 530/334 |
| 5,015,845 | A | 5/1991 | Allen et al. ................ 250/288 |
| 5,045,694 | A | 9/1991 | Beavis et al. .............. 250/287 |
| 5,071,909 | A | 12/1991 | Pappin et al. ............. 525/54.1 |
| 5,077,195 | A | 12/1991 | Blalock et al. ............. 435/6 |
| 5,143,852 | A | 9/1992 | Valkirs et al. ............. 436/501 |
| 5,160,840 | A | 11/1992 | Vestal ........................ 250/287 |
| 5,175,430 | A | 12/1992 | Enke et al. ................ 250/282 |
| 5,175,431 | A | 12/1992 | Eisele et al. .............. 250/288 |
| 5,208,458 | A | 5/1993 | Busch et al. ............... 250/288 |
| 5,240,616 | A | 8/1993 | Kato et al. ................. 210/656 |
| 5,252,216 | A | 10/1993 | Folena-Wasserman et al. .. 210/635 |
| 5,266,684 | A | 11/1993 | Rutter et al. ............... 530/334 |
| 5,270,163 | A | 12/1993 | Gold et al. ................. 435/6 |
| 5,270,170 | A | 12/1993 | Schatz et al. ............ 435/7.37 |
| 5,272,337 | A | 12/1993 | Thompson et al. ........ 250/288 |
| 5,281,397 | A | 1/1994 | Ligon et al. ............... 422/89 |
| 5,285,064 | A | 2/1994 | Willoughby ............... 250/288 |
| 5,288,644 | A | 2/1994 | Beavis et al. .............. 436/94 |
| 5,302,532 | A | 4/1994 | Lau ........................... 436/528 |
| 5,306,619 | A | 4/1994 | Edwards et al. ............ 435/6 |
| 5,313,061 | A | 5/1994 | Drew et al. ................ 250/281 |
| 5,340,474 | A | 8/1994 | Kauvar ..................... 210/198.2 |

FOREIGN PATENT DOCUMENTS

| EP | 411503 | 2/1991 |
| EP | 0 614 989 A1 | 9/1994 |
| WO | WO93/07168 | 4/1993 |
| WO | WO 94/06017 | 3/1994 |
| WO | WO 94/14824 | 7/1994 |
| WO | WO94/15951 | 7/1994 |
| WO | WO 94/19694 | 9/1994 |

OTHER PUBLICATIONS

Wiesmeüller et al., "Novel Low–Molecular–Weight Synthetic Vaccine Against Foot–and–Mouth Disease Containing a Potent B–Cell and Macrophage Activator," *Vaccine*, 7:29–33 (Feb. 1989).

W. Kopuciewicz and F. F. Regnier. "A System for Coupled Multiple–Column Separation of Proteins," *Analytical Biochemistry*, 129:472–482 (1983).

Waksman et al., "Binding of a High Affinity Phosphotyrosyl Peptide to the Src SH2 Domain: Crystal Structures of the Complexed and Peptide–Free Forms," *Cell*, 72:779–790 (Mar. 12, 1993).

Michael Famulok and Jack W. Szostak, "In Vitro Selection of Specific Ligand–Binding Nucleic Acids," *Angew. Chem. Int. Ed. Engl.*, 31:979–988 (1992).

(List continued on next page.)

Primary Examiner—Bennett Celsa
(74) Attorney, Agent, or Firm—Testa, Hurwitz & Thibeault, LLP

(57) ABSTRACT

The invention provides novel methods for screening a sample to select a ligand to a target of interest and for obtaining information about the ligand and its binding characteristics. Specifically, the claimed multi-dimensional methods involve combining a solution of heterogeneous ligands with the target of interest to screen the ligands on the basis of one or more binding characteristics. Ligands having the first binding characteristic bind to the target of interest thereby to form a target/ligand complex. The complex then optionally is separated from the unbound components using any of a variety of separation techniques, e.g., size exclusion. At least one of the complex or unbound components then is introduced to a second "dimension". The second dimension is capable of separating components based upon a second binding characteristic. One then elutes the ligand having the desired binding characteristics.

18 Claims, 11 Drawing Sheets

OTHER PUBLICATIONS

Kassel et al., "Evaluation of Packed Capillary Perfusion Column HPLC/MS/MS for the Rapid Mapping and Sequencing of Enzymatic Digests," *Analytical Chemistry* 66(2):236–243 (Jan. 15, 1994).

Mandana Sassanfar & Jack W. Szostak,"An RNA Motif that Binds ATP," *Letters To Nature*, pp. 550–553 (1993).

Gordon W. Niven and Peter G. Scurlock, "A Method for the Continuous Purification of Proteins by Affinity Adsorption," *J. of Biotechnology*, 3:179–190 (1993).

Huddleston et al., "Selective Detection of Phosphopeptides in Complex Mixtures by Electrospray Liquid Chromatography/Mass Spectrometry," *J. Am Soc Mass Spectrom*, 4:710–717 (1993).

Mark A. Schenerman and Tedd J. Collins, "Determination of a Monoclonal Antibody Binding Activity Using Immuno-Detection," *Analytical Biochemistry*, 217:241–247 (1994).

Afeyan et al., "Automated Real–Time Immunoassay of Biomolecules," *Nature*, 358:603–604 (Aug. 1992).

Tim Clackson and James A. Wells, "In Vitro Selection From Protein and Peptide Libraries." *Tibtech*. 12:173–184 (May 1994).

Dan Medynski, "Synthetic Peptide Combinatorial Libraries," *Bio/Technology*, 12:709–710 (Jul. 1994).

Wyatt et al, "Combinatorial Selected Guanosine–Quartet Structure is a Potent Inhibitor of Human Immunodeficiency Virus Envelope–Mediated Cell Fusion," *Proc. Natl. Acad. Sci. USA*, 91:1–5 (1994).

Marks et al., "Molecular Evolution of Proteins on Filamentous Phage," *J. of Biological Chemistry* 267:16007–16010 (Aug. 15, 1992).

Marks et al., "Human Antibody Fragments Specific for Human Bolld Group Antigens from a Phage Display Library," *Bio/Technology*, 11:1145–1149 (Oct. 1993).

Keough et al., "Antisense DNA Oligonucleotides II: the Use of Matrix–Assisted Laser Desorption/Ionization Mass Spectrometry for the Sequence Verification of Methylphosphonate Oligondeoyribonucleotides," *Rapid Communications in Mass Spectrometry*, 7:195–200 (1993).

Jamie K. Scott and Lisa Craig, "Random Peptide Libraries," *Analytical Biotechnology*, 5:40–48 (1994).

Richard A. Houghten, "Peptide Libraries—Criteria and Trends," *Trends In Genetics*, 9(7):235–239 (Jul. 1993).

Günther Jung and Annette G. Beck–Sickinger. "Multiple Peptide Synthesis Methods and Their Applications," *Angewandte Chemin Int. Ed. Engl.* 31:367–383 (1992).

Giorgio Fassina, "Oriented Immobilization of Peptide Ligands on Solid Supports," *J. of Chromatography*, 591:99–106 (1992).

Collet et al., "A Binary Plasmid System for Shuffling Combinatorial Antibody Libraries," *Proc. Natl. Acad. Sci. USA*. 89:10026–10030 (1992).

Lam et al., "Rational Design of Potent, Bioavailable, Nonpeptide Cyclic Ureas as HIV Protease Inhibitors," *Science*, 263:380–384 (Jan. 1994).

Joly et al., "Disruption of PDGF Receptor Trafficking by Mutation of Its PI–3 Kinase Binding Sites," *Science*, 263:684–686 (Feb. 1994).

Regan et al., "Purification and Characterization of the Human Platelet $\alpha_2$–Adrenergic Receptor," *J. of Biological Chemistry*, 261:3894–3900 (1986).

Lomasney et al., "Mammalian $\alpha_1$–Adrenergic Receptor," *J. of Biological Chemistry*, 261(17):7710–7716 (1986).

Kang et al., "Antibody Redesign by Chain Shuffling from Random Combinatorial Immunoglobulin Libraries," *Proc. Natl. Acad. Sci. USA*. 88:11120–11123 (1991).

Cerione et al., "Functional Reconstitution of the $\alpha$2–Adrenergic Receptor with Guanine Nucleotide Regulatory Proteins in Phospholipid Vesicles." *J. of Biological Chemistry*, 261(8):3901–3909 (1986).

James W. Putney Jr., "Excitement About Calcium Signaling in Inexcitable Cells," *Science*, 262:676–678 (Oct. 1993).

Raff et al., "Programmed Cell Death and the Control of Cell Survival: Lessons from the Nervous System," *Science*, 262:695–700 (Oct. 29, 1993).

Lovejoy et al., "Structure of the Catalytic Domain of Fibroblast Collagenase Complexed with an Inhibitor," *Science*, 263:375–377 (Jan. 21, 1994).

Wiodawer et al., "Hematopoietic Cytokines: Similarities and Differences in the Structures, with Implications for Receptor Binding," *Protein Science*, 2:1373–1382 (1993).

Donald Van Dyke, "Software to Increase the Speed of DNA Sequence Assembly," *Sequencing and Synthesis/Application Note*, pp. 11–12 (Oct. 1993).

Richard Peters and Robert C. McKinstry, "Three–Dimensional Modeling and Drug Development," *Bio/Technology*, 12:147–150 (Feb. 12, 1994).

Dr. Allen K. Murray, "Molecular Models in Enzyme Specificity Studies," *Scientific Computing & Automation*, pp. 23–26 (Aug. 1993).

Stephen M. Edgington, "Neuronal Signal Transduction: Will Controlling Phosphorylation Cure Disease?," *Bio/Technology*, 11:1237–1241 (Nov. 1993).

Stringham et al., "Selective Non–Adsorption Preparative Chromatography: An Examination of Throughput, Mobile Phase Selection and Alternative Modes of Separation," *Preparative Chromatography*, 1(2):179–193 (1989).

Nigel Beeky, "Peptidomimetics and Small–Molecule Drug Design: Towards Improved Bioavailability and in vivo Stability," *Tibtech*. 12:213–216 (1994).

Wieslaw M. Kazmierski, "Recent Advances in the Design and Synthesis of Small–Molecular Mimetic Drugs." *Tibtech*. 12:216–218 (Jun. 1994).

Pieles et al., "Matrix–Assisted Laser Desorption Ionization Time–of–Flight Mass Spectrometry: A Powerful Tool for the Mass and Sequence Analysis of Natural and Modified Oligonucleotides," *Nucleic Acids Research*, 21(14):3191–3196 (1993).

Djojonegoro et al., "Bacteriophage Surface Display of an Immunoglobulin–Binding Domain of Staphylococcus Aureus Protein A," *Bio/Technology*, 12:169–172 (Feb. 1994).

Stierandova et al., "Peptide–Encoding for Structure Determination of Nonsequenceable Polymers Within Libraries Synthesized and Tested on solid–Phase Supports," *Peptide Research*, 6(3):161–170 (1993).

Lam, et al., "Rational Design of Potent, Bioavailable, Nonpeptide Cyclic Ureas as HIV Protease Inhibitors," *Science*, 263:380–384 (Jan. 21, 1994).

David G. Alberg and Stuart L. Schreiber, "Structure–Based Design of a Cyclophilin–Calcineurin Bridging Ligand," *Science*, 262:248–250 (Oct. 8, 1993).

Robert L. Stevenson, "ISPPP '94," *Application Note*, pp. 41–42 (Apr. 1995).

Songyang et al., "SH2 Domains Recognize Specific Phosphopeptide Sequences," *Cell*, pp. 767–778 (1993).

Susan I. Danheiser, "Structure–Based Small Molecule Design Emerges as Key Biotech Drug Development Strategy," *Genetic Engineering News*, p. 1, p. 36 (Jul. 1993).

Jenison et al., "High–Resolution Molecular Discrimination by RNA," *Science, 263:*1425–1429 (Mar. 11, 1994).

Moyle et al., "Co–Evolution of Ligand–Receptor Pairs," *Nature, 368:*251–255 (Mar. 17, 1994).

Peter J. Schatz, "Use of Peptide Libraries to Map the Substrate Specificity of a Peptide–Modifying Enzyme: a 13 Residue Consensus Peptide Specifies Biotinylation in *Escherichia Coli,*" *Bio/Technology 11:*1138–1143 (Oct. 1993).

Jeffrey W. Jacobs and Stephen P. A. Fodor, "Combinatorial Chemistry–Applications of Light–Directed Chemical Synthesis," *Tibtech, 12* (Jan. 1994).

Chait et al., "Protein Ladder Sequencing," *Science, 262:*89–92 (Oct. 1, 1993).

Furka et al., "General Method for Rapid Synthesis of Multicomponent peptide Mixtures," *Peptide & Protein Research, 37:*487–493 (1991).

Deres et al., "In Vivo Priming of Virus–Specific Cytotoxic T Lymphocytes with Synthetic Lipopeptide Vaccine," *Nature, 342:*561–564 (Nov. 30, 1989).

Yarovsky et al., "High Performance Liquid Chromatography of Amino Acids. Peptides and Proteins." *J. of Chromatography, 660:*75–84 (1994).

Banner et al., "A Method for Characterization of Endogenous Ligands to Orphan Receptors Belonging to the Steroid Hormone Receptor Superfamily—Isolation of Progesterone from Pregnancy Plasma Using Progesterone Receptor Ligand–Binding Domain," *Analytical Biochemistry, 200:*163–170 (1992).

Youngquist et al., "Matrix–Assisted Laser Desorption Ionization for Rapid Determination of the Sequences of Biologically Active Peptides Isolated From Support–Bound Combinatorial Peptide Libraries," *Rapid Communications in Mass Spectrometry, 8:*77–81 (1994).

Brooks Shera, "Speed Sorts Molecules," *Inside R & D.* 22(35):1–2 (Sep. 1, 1993).

Stringham et al., "Selective Non–Adsorption Preparative Chromatography: An Examination of Throughput, Mobile Phase Selection and Alternative Modes of Separation," *Preparative Chromatography, 1*(2):179–193 (1989).

Stefan Stevanovic and Güther Jung, "Multiple Sequence Analysis: Pool Sequencing of Synthetic and Natural Peptide Libraries," *Analytical Biochemistry, 212:*212–220 (1993).

Steven A. Benner, "Catalysis: Design Versus Selection," *Science, 261:*1402–1403 (Sep. 10, 1993).

Edward J. Reber and Carl O. Pabu, "Zinc Finger Phage: Affinity Selection of Fingers with New DNA–Binding Specificities," *Science, 263:*671–673 (Feb. 4, 1994).

Chaiken, IM, "Analytical Affinity Chromatography In Studies Of Molecular Recognition In Biology: A Review," *J. Chromatogr.* 376:11–32 (1986).

Kerr, JM et al., "Identification Of Antibody Mimotopes Containing Non–Natural Amino Acids by Recombinant And Synthetic Peptide Library Affinity Selection Methods," *Bioorg. Med. Chem. Lett.* 3:463–468 (1993).

Zuckermann, RN et al., "Identification Of Highest–Affinity Ligands By Affinity Selection From Equimolar Peptide Mixtures Generated By Robotic Synthesis," *Proc. Natl. Acad. Sci. USA, 89:*4505–4509 (1992).

Chen, Z. et al., "Identification Of A Soluble Salicylic Acid–Binding Protein That May Function In Signal Transduction," *PNAS, 88:*8179–8183 (1991).

Lu et al., "The Identification and Characterization of Collagen Receptors Involved in HeLa Cell–Substratum Adhesion," *J. Biol. Chem., 264*(23):13546–13558 (1989).

Houghton et al., "The Use of Synthetic Peptide Combinatorial Libraries for the Identification of Bioactive Peptides," *Biotechniques, 13*(3): 412–421 (1992).

Houghten, "Soluble Combinatorial Libraries: Extending the Range and Repertoire of Chemical Diversity," *Methods: A Companion to Methods in Enzymology, 6:*354–360 (1994).

Janis et al., "Dual–Column Immunoassays Using Protein G Affinity Chromatography," *Anal. Chem. 61:*1901–1906 (1989).

Fassina et al., "Design of hydropathically complementary peptides for Big Endothelin affinity purification," *Int. J. Peptide Res. 39:*540–548 (1992).

Ghosh et al., (Abstract), "Reversed Phase Extraction Chromatographic Study of Copper–II with a High Molecular Weight Carboxylic Acid and Its Analytical Applications," *Indian J. Chem. Sect. A. Inorg. Phys. Theor. Anal., 28*(9):814–816 (1989).

Pawlowski et al., "Overexpression and mutagenesis of the cDNA for rat liver 3–alpha–hydroxysteroid/dihydrodioledhydrogenase: Role of cysteines and tyrosines in catalysis," *J. of Biol. Chem. 269:*13502–13510 (1994) (Astract).

IDENTIFICATION OF PEPTIDE SEQUENCES
BINDING TO CONCANAVALIN A IN A
SUGAR-SPECIFIC MANNER*

RANKING AMINO ACIDS FROM GREATEST TO LEAST ENRICHMENT OVER CONTROL

NO INCUBATION ON-COLUMN

| CYCLE # | | | | |
|---|---|---|---|---|
| 1 | H | R | Q | N |
| 2 | H | N | Q | |
| 3 | R | H/D/Q/N | | |
| 4 | S | R | W | Y |
| 5 | Y | R | Q | |

30MIN INCUBATION ON-COLUMN

| CYCLE # | | | | | | | |
|---|---|---|---|---|---|---|---|
| 1 | W | H | Q | R | I | V | N |
| 2 | W | V | T | Q | I | P | |
| 3 | W | V | T | Q | D | E | |
| 4 | W | S | Q | V | E | N | |
| 5 | V | T | W | Q | E/D/G | N | R |

*TABLE SHOWING ENRICHMENT OF AMINO ACIDS AT EACH CYCLE IN THE ABSENCE AND PRESENSE OF SUGAR

FIG. 8

HIGH SPEED, AUTOMATED, CONTINUOUS FLOW, MULTI-DIMENSIONAL MOLECULAR SELECTION AND ANALYSIS

RELATED APPLICATION

This application is a divisional of application Ser. No. 09/267,993, filed on Mar. 12, 1999, now U.S. Pat. No. 6,358,692 which is a continuation of Ser. No. 08/670,670, filed on Jun. 26, 1996, now abandoned, which claims the benefit of Ser. No. 60/000,518, filed on Jun. 26, 1995, now expired, the entire disclosures of which are incorporated by reference herein.

FIELD OF THE INVENTION

This invention relates to the integrated, multi-dimensional, rapid analysis of solutions of a large number of mixed molecular species, commonly called "libraries". More specifically, the invention is directed toward methods for the discovery of molecular entities useful in a variety of biological contexts using hi-flux screening of natural and synthetic libraries to select ligands having a desired affinity for a target molecule of interest.

BACKGROUND

Multi-dimensional systems, i.e., systems involving the application of multiple distinct physico-chemical separation steps, are (n)own to be useful for many applications. The purification of proteins, for example, frequently is accomplished using multiple passes through different chromatographic columns exploiting differential partitioning such as adsorption and size exclusion. Inherent in any multi-dimensional process is the necessity to identify the desired component, from the output of the first partition, to collect it, and to introduce it into the next dimension of the system. Disadvantages of such systems include slow analysis, solvent incompatibility between successive partitioning phases, the necessity of labor intensive handling, and consequent contamination or loss of sample.

The recent prior art discloses various new methods for implementing the search for novel agents such as, for example, pharmacological or therapeutic agents (i.e., drug discovery) agents useful in animal care or management, agriculturally useful chemicals, selective biocides for insects, weeds, or other pests, and catalytic and other entities useful in industrial processes. Collections of molecules or "libraries" are prepared and screened for molecules having a specified bioactivity, as indicated initially by detection of binding between one or more species or "ligands" in the library and a "target" molecule with which it reacts to influence some biological process. More specifically, libraries consist of a complex assortment of molecules containing one or more ligands which may bind to a target of interest. The identification of ligands which bind may provide a lead for identifying compounds with a desired biological activity, e.g., as a potential drug candidate. As methods have become available to screen these complex mixtures more effectively, interest in exploiting this new "rational design" or "directed molecular evolution" approach has increased.

Libraries of biopolymers may be prepared by the sequential synthesis based on randomized addition of amino acid, nucleotide, or sugar residues, or combinations thereof, to form peptides, RNAs, polysaccharides, glycosaminoglycans or the like, thereby to prepare a random mixture of oligomers. Techniques suitable for preparing protein or peptide libraries at the nucleic acid level by phage display and similar technologies also are known. Likewise, these general synthesis approaches could be adapted to prepare, peptide nucleic acid (PNA) libraries, or libraries of PNA/DNA, or PNA/RNA chimeras, and indeed other complex mixtures of synthetic molecules.

Screening of soluble peptide libraries frequently is performed either by immunoassay or by laboriously assaying for a particular biological function (e.g. blocking of viral replication). These methods are not necessarily target based and in most cases, involve tedious set up. See Scott and Craig, Curr. Opin. Biotech. 5, 40–48 (1994); Dooley et. al. Proc. Natl. Acad. Sci., 90:10811–10815 (1993); Dooley et. al., Life Sciences, 92:1509–1517 (1990); Houghton et. al., Biorg. Med. Chem. Lett., 3:405–412 (1993). For example, inhibitors of HIV protease have been identified by screening sets of equimolar peptide mixtures, together containing more than 240,000 soluble tetrapeptides. See Owens et. al. Biochem. Biophys. Res. Comm., 181:402–408 (1991). It has also been suggested to use a phosphopeptide library to determine the sequence specificity of the peptide-binding sites of SH2 domains by employing the GST-SH2 fusion protein immobilized onto a column. See Songyang et al. Cell, 72, 767–778 (1993).

The screening methods described immediately above are based upon identifying which ligand in a mixture binds to a target of interest. Binding typically is assayed with either the ligands of the library or the target immobilized on some form of solid support. Various solution parameters may be adjusted to emulate different binding conditions and to obtain different ligands. Often, peptides which are obtained through procedures involving their immobilization to a support have disappointing affinity, i.e., have a binding constant too low to be useful. Traditionally, antibodies are used for the affinity purification of proteins and other biomolecules. However, the cost of generating antibodies, the potential for antibody leaching, and the need for relatively harsh eluting conditions pose problems for the routine use of antibodies in affinity purification.

Screening methods known in the art thus are not entirely satisfactory. Prior methods for detecting or identifying ligands which bind to a target of interest often fail to provide ligands of sufficiently high affinity to be useful, and additionally suffer from the loss of sample, the need for large amounts of ligands, and the need to vary loading, binding, or elution conditions to obtain useful results. Additionally, existing systems are unable selectively to screen a library while simultaneously determining the affinity of selected ligand(s) for the target under relevant conditions.

A major hurdle in the exploitation of current screening techniques of the type described above is effective chemical characterization of ligands identified in these processes. Chemical characterization, e.g., determining the sequence of an identified biopolymer, is at best time-consuming and complex. A major focus of prior art screening techniques is to enable the collection of enough of or enough information about a ligand of interest so as to permit determination of its structure and to enable synthesis of larger amounts for testing and further empirical structural refinement.

Accordingly, there is a need for integrated, multi-dimensional screening, selection and analysis systems and methods which permit automated, direct transfer of samples without dilution or loss between various dimensions, and efficiently screen for, and subsequently permit characterization and recovery of ligands to a target of interest, even when present at low concentration.

SUMMARY OF THE INVENTION

Accordingly, the present invention is directed to rapid, efficient and automated, multi-dimensional systems, methods and apparatus for screening libraries to select, recover and characterize a candidate ligand with a desired or preselected affinity K for a preselected target molecule. Additionally, the present invention is directed to certain combination of individual dimensions of such a system, which can be used to obtain a desired result, and, specifically to a method of detecting a ligand to a target of interest which overcomes the disadvantages of the methods known in the art.

Additional features and advantages of the invention will be set forth in the description which follows, and in part will be apparent from the description and drawing, or may be learned by practice of the invention. The objectives and other advantages of the invention will be realized and attained by the process particularly pointed out in the written description, drawing, and appended claims.

To achieve these and other advantages, and in accordance with the invention as embodied and broadly described, the invention provides novel methods for screening a sample to select a ligand to a target of interest and for obtaining information about the ligand and its binding characteristics. Specifically, the claimed multi-dimensional methods involve combining a solution of heterogeneous ligands with the target of interest to screen the ligands on the basis of one or more binding characteristics. Ligands having the first binding characteristic will bind to the target of interest thereby to form a target/ligand complex. The complex then optionally is separated from the unbound components using any of a variety of separation techniques, e.g., size exclusion. At least one of the complex or unbound components then is introduced to a second "dimension". The second dimension is capable of separating components based upon a second binding characteristic. One then elutes the ligand having the desired binding characteristics.

Additionally, the invention relates to a method of detecting the presence of a ligand having a desired or preselected affinity (K) for a preselected target molecule in a sample of ligands in a solvent by loading a column with a known concentration of target molecules (T), and passing the sample through the column so that ligands in the sample bind to the column through the target molecule. A series (n) of column volumes of solvent then are passed through the column, where n is a number of column volumes between 1 and 10,000. A subset of the column volumes exiting the column is passed through a ligand accumulator to immobilize on the accumulator ligands having the preselected affinity K. Ligands having the preselected affinity then can be eluted from the accumulator, and, optionally, identified, and/or synthesized in commercial quantities.

In another aspect, the invention relates to a method of separating mixed species of ligand dissolved in a solvent into separate fractions of ligands, wherein each fraction is characterized by a different affinity or range of affinities for a preselected target molecule. Initially, the mixed ligand species are passed through a column comprising immobilized target molecules so that the ligands will bind to the target. A series of column volumes of solvent then are passed through the column, and at least two subsets of the column volumes of solvent exiting the column are then passed through a ligand accumulator, thereby immobilizing ligands characterized by separate ranges of affinity constants. The fractions containing ligands characterized by different ranges of affinities are then optionally eluted from the accumulator to separate them chemically for further screening or analysis.

In yet another embodiment, the invention relates to a multi-dimensional system or apparatus for obtaining and identifying ligands having a preselected affinity for a target of interest. The multi-dimensional system consists of at least two dimensions, the first comprises a chromatographic element to which a concentration, preferably a known concentration T, of target molecules of interest is bound. The system has as a second dimension another chromatographic element followed by a detector. Additionally the system in some embodiments has an interface between each dimension, and a controller for automatically regulating the various dimensions of the system.

In yet other embodiments, the apparatus comprises multiple valves, a first column with target molecules immobilized thereon; an accumulator or separate column to receive at least a portion of the exist stream of the first column, an optional interface to condition the exit stream to make it compatible with the accumulator or second column, and a detector such as a mass spectrometer. The interface may, in some embodiments include a buffer exchange such as a mixed bed ion exchanger, a cation exchanger or an anion exchanger, and means to inject solvent so that the pH, ionic strength, etc. can be controlled so as to permit further downstream partitioning of partly screened ligand species.

The ability of the methods and apparatus of the invention to provide for continuous flow through multiple partitioning dimensions is dependent in many cases on the use of interface columns. These condition the solvent containing the dissolved ligands exiting an upstream column for effective partitioning in a downstream column. In one such interface, effluent high in salt is desalted by passage through a reverse phase column. The ligands adsorb, the salt is washed out, and the ligands then are eluted with salt-free or low salt solvent. In another, organic solvent such as acetonitrile is removed by passing the solution through an ion exchange column, binding the ligands therein, and subsequently eluting with an aqueous eluant. In still another, the pH of acidic solvents is increased by binding in a cation exchange resin, washing out the acid, and eluting in, e.g., a neutral pH solvent. Similarly, the pH of alkaline solvents may be decreased by binding in an anion exchange resin.

In yet other embodiments, the invention features an interface for sampling a liquid chromatographic (LC) exit stream, and delivering the sample to a mass spectrometer (MS). The sampler has a predetermined sample volume disposed, for example, in a sample loop, alternatively switchable to extract from an LC exit stream, and to insert into an analysis stream of an MS. A sample controller cycles the sampler to first extract and then to insert the sample. In various embodiments, the sampler can comprise a multi-port valve and the sample volume is disposed within tubing of a predetermined volume. The sample controller may cycle the sampler to take a sample of the LC eluate a plurality of times during an LC analysis peak. Other embodiments may include a second sampler. The first and second samplers can be placed in series.

The embodiments of the methods, apparatus and system of the invention described above may optionally include a detector for identifying a selected ligand. The detector may consist of, for example, a mass spectrometer or a fluorescence detector.

Additionally, in other embodiments, the invention relates to a method of detecting a ligand having a desired high affinity K for a preselected target molecule when the ligand and the target are present together in preselected solvent conditions. The ligand to be detected may be one of a multiplicity of ligand species in a heterogeneous sample. The method involves immobilizing the target molecule onto a column, passing the sample through the column to promote binding of ligands in the sample to the target molecules, and then passing a series of column volumes of a solvent defining the solvent conditions. A subset (kp) of the column volumes exiting the column are then passed through a ligand accumulator to immobilize thereon ligands having the desired affinity, and then those ligands are eluted. A selected ligand may be characterized by a high affinity K for the target molecule equal approximately (kp)/T, where T is the concentration of target molecules in the column. In some instances, the conditions under which the sample is passed through the column (i.e. to promote binding of ligands to target molecules) is different from the preselected solvent conditions.

In other embodiments, the methods of the invention relate to the detection of ligand having a high on-rate, Ko, when said ligand and said target molecule are present together in preselected solvent conditions. The ligand is detected in a sample comprising multiple ligand species, at least one of which binds a preselected target molecule with an affinity of at least about $10^4 M^{-1}$. The target molecule is immobilized onto a column, and the sample is provided in a sample defining the preselected solvent conditions. The sample is passed through the column at a high linear fluid velocity so as to minimize the residence time of the ligands in the column, thus selectively binding high on-rate ligands to the target molecules, in preference to other ligands in the sample. One can then elute the column to obtain an output, and identify the high on-rate ligands. Optionally, the output can be passed through a ligand accumulator, which is then eluted to produce an output rich in a high on-rate ligand.

In other embodiments, the invention relates to a method of selecting ligands to a target of interest on the basis of the off-rate of the ligand.

The methods of the invention in certain aspects relate also to a method for detecting a ligand having a high affinity for a target molecule by providing a library obtained by the digestion of one or more proteins or other biopolymers. The sample solution and a target molecule are combined under conditions which allow suitable ligands, if present, to bind to the target; and thereafter the ligands which bind to the target (forming a complex) are separated from those which do not bind. The sample solutions may be obtained by the digestion of any protein, including post-translationally modified proteins, antibodies, etc.

The methods of the claimed invention also relate to detecting a ligand in a library which will bind when the ligand and the target molecule are present together in preselected solvent conditions, e.g., physiological saline. As before, a target molecule is immobilized onto a column, and the sample is passed through the column under the preselected solvent conditions. Next, a series of column volumes of solvent is passed through the column to select a desired ligand. The eluate is then introduced to a ligand accumulator.

The methods also relate to the preparation of pharmaceutically active compositions using the multi-dimensional methods described above, and to the subsequent commercial production of such compositions.

In yet other aspects, the invention relates to methods of selecting ligands based upon one or more binding characteristics by the use of multiple dimensions.

In an important aspect, the invention provides apparatus and methods which are automated, fast, operate by continuous flow. The methods are capable in preferred embodiments of selecting ligands having affinity and specificity for essentially any target molecule, separating the members of the select group from one another, and obtaining physicochemical data characteristic of the structure of the selected ligands. The nature of the library useful in the system essentially is unlimited. Thus, mixtures of organic compounds may be used. Digests of biopolymers, either natural or synthetic, are particularly attractive. Such digests may comprise mixtures of peptides, polysaccharides, polynucleotides, various derivatized forms thereof, and variously sized fragments thereof. The biopolymers may be extracted from plant or animal tissues, diseased or healthy, digested if necessary, or used as is. Such libraries are available in abundance, easy to prepare, may be of lower toxicity and more stable than synthetic peptides, and may be varied and screened systematically.

It is to be understood that both the foregoing general description and the following detailed description are exemplary and explanatory and are intended to provide further explanation of the invention as claimed.

BRIEF DESCRIPTION OF THE DRAWINGS

FIG. 8 identifies peptide sequences binding to concanavalin A in a sugar-specific manner.

DETAILED DESCRIPTION OF THE INVENTION

Definitions

Figure 1:
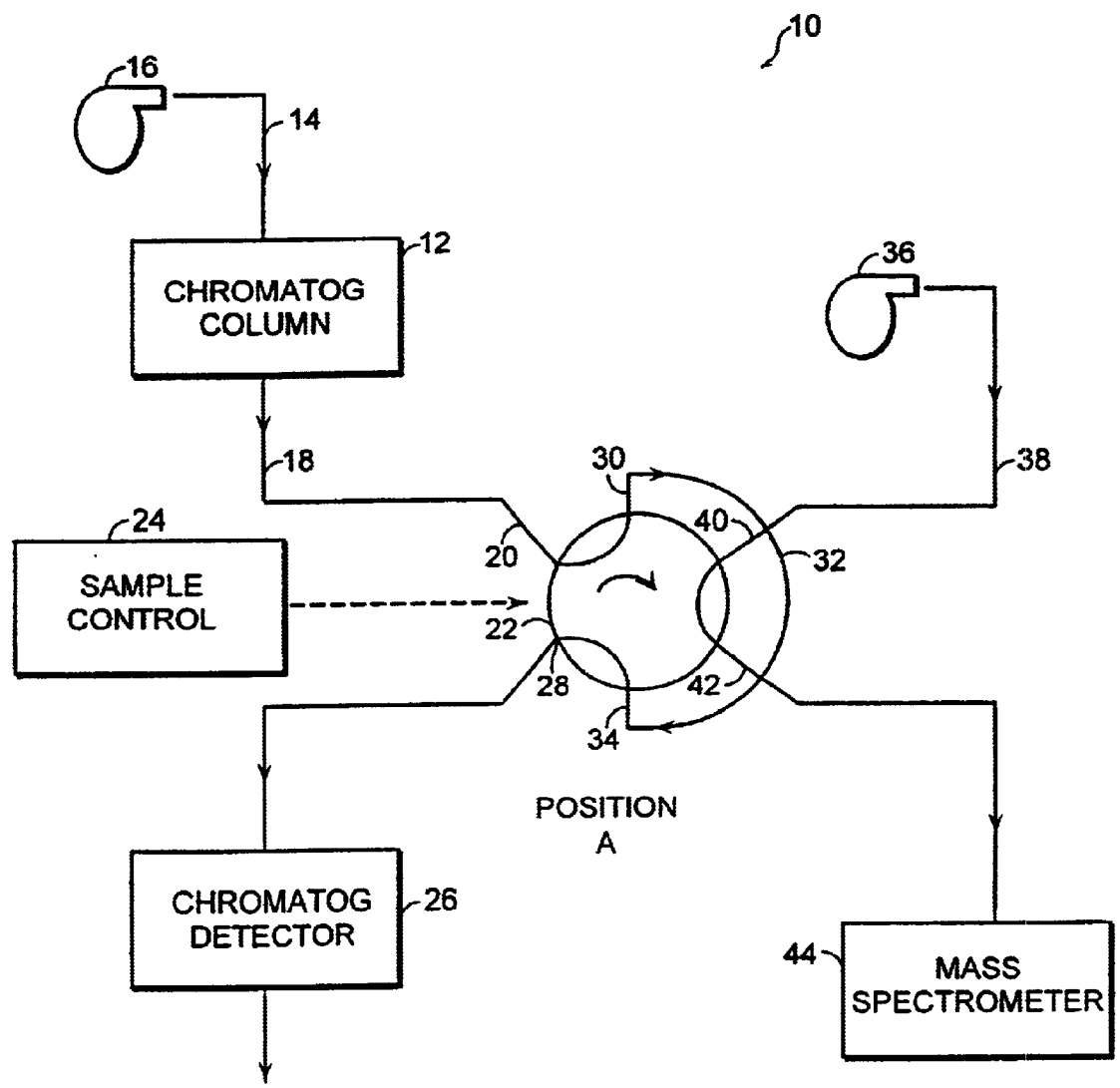
FIG. 1 is a schematic representation of one embodiment of the apparatus of the invention.

| | |
|---|---|
| Accumulator | a column designed to non-specifically adsorb ligands and optionally and preferably to permit the separation of the adsorbed ligands by elution. |
| Affinity Column | a column containing immobilized target molecules accessible to ligands passing therethrough so as to permit formation of complex. |
| Biopolymer | a polymeric molecule of biological origin comprising plural attached monomers, derivatized or not, including amino acids, DNAs, RNAs, PNAs, sugar residues, or combinations thereof. |
| Column | used broadly herein to refer to laboratory scale or microscale chromatography columns, i.e., pipes packed with porous or nonporous, rigid or gel particles, or containing one-piece matrices, designed for chromatographic separation, or functional equivalents of such columns including membranes and capillaries or bundles of capillaries. |
| Complex | a non-covalent association of a candidate ligand and a target molecule. |
| Continuous Flow | systems wherein impelled solutions containing ligands impelled by a pump are passed sequentially through various columns, valves, detectors, interface units, etc. within the system without requiring collection or separate analysis manually or robotically until the solution exits the system. |
| Eluate | the fraction of liquid exiting a column containing solutes that were sorbed on the column and then desorbed by various types of elution, including gradient elution and isocratic elution techniques, and elution by changing pH, ionic strength, or other parameters of solutions within the column, or simply by passing a large volume of buffer through the column. |
| Exit Stream | a collective term referring to either the portion of liquid exiting a column containing solutes which failed to bind to the column or an eluate. |
| Library | a collection of structurally distinct ligand species comprising intact or fragmented organic molecules or molecules of biological origin such as peptides, nucleotides, polysaccharides, and various derivatized forms thereof. |
| Ligand | a generic term referring to the structurally distinct chemical species that are dissolved in a solvent and constitute a library. |
| Mass spectrometer | a machine adapted for the introduction of microsamples containing a selected ligand or fragments of a ligand, or which generates ligand fragments, and measures the mass to charge ratio of solutes in the sample to provide data helpful or sufficient to determine the structure of the ligand. |
| MS/MS | a mass spectrometer detector of the type that determines the mass to charge ratio both of a ligand inserted therein and then of fragments of that ligand generated by ionization or otherwise. |
| Reverse Phase | a chromatography surface characterized by an abundance of hydrophobic moieties. |
| Target Molecule | a compound such as a receptor, enzyme, DNA, RNA, etc. comprising either a) the moiety to which a selected ligand will bind with at least some selectively and reasonably high affinity, i.e., is the molecule which will be exploited during use of the selected ligand, or b) is a moiety which the selected ligand is selected specifically not to bind, so as to avoid cross reactivity or the like. |

I. Nature of Library

A "library" as used herein encompasses virtually any solution of compounds to be screened for a ligand having an activity of interest. The library may, for example, comprise a natural or synthetic combinatorial library; solutions obtained naturally, such as from body fluids, plant fluids; or virtually any other natural or synthetic substances which can be put into solution and detected by a physical or chemical characteristic. Thus there are limitless sample possibilities and the skilled artisan can choose a sample based upon his particular application.

In various embodiments it is preferable to use a natural library of molecules obtained by the digestion of one or more natural substances. When screening for lead compounds for pharmaceutical applications (i.e. drug discovery), the sample may be obtained by the digestion of one or more molecules obtained from the host organism. It may be preferable to digest a molecule indigenous to the host which has the desired biological activity. The inventors have discovered that these libraries have a high likelihood of containing a fragment having the desired activity against a target of interest.

Natural libraries may be prepared by enzymatic digestion or other manipulation of a sample prior to screening, or in certain instances, may be a solution as found in nature without prior manipulation. The use of proteolytic enzymes to generate peptides of pre-existing amino acid sequences through simple degradation of existing proteins is well known. (U.S. Pat. No. 3,855,196; Pieczenik, WO87/01374; U.S. Pat. No. 5, 366,862) Preferably one may digest the target molecule or a related molecule to create a library of potential ligands related to the target peptide. Thus, if one desired a ligand which binds with a preselected affinity to a growth hormone, a library of potential ligands could be prepared by digesting a known ligand to the growth hormone, and then screening for the desired ligand. For example, one may obtain proteolytic digests of mixtures of common proteins that are commercially available from a company such as SIGMA. These mixtures are referred to as either natural tryptic peptide mixtures or natural tryptic/chymotryptic peptide mixtures. Similarly, one may, for example, raise polyclonal antisera to a preselected target molecule, and digest the immunoglobulin in the sera to produce a mixture of candidate ligands.

Additionally the invention contemplates the use of natural libraries which have not been subjected to digestion prior to screening. Thus, one may obtain a sample by extracting animal or plant cells, tissue or fluids such as body fluids such as saliva, semen, vaginal fluids, and blood, as well as a naturally occurring libraries such as a cellular lysate or fermentation broths. Such libraries may optionally be manipulated by various processes prior to screening.

Such naturally obtained libraries are advantageous for a number of reasons. First, the likelihood of identifying a ligand which will be toxic to a host is diminished if the library is created by enzymatic digestion using typsin or chymotrypsin, for example, as these enzymes are found in the human body and are thus unlikely to have toxic effects. Second, since, for example, many proteins are post-translationally modified, one can obtain fragments having these modifications. This is especially beneficial in applications where the modification is involved in the biological activity of the molecule or fragment. Such post translationally modified proteins may include, for example proteins which are sulfated, amidated, carboxylated, phosphorylated, disulfide bonded, or lipidated.

II. The Multidimensional Approach

A. Theoretical Basis for Screening

Peptide combinatorial libraries and natural proteolytic mixtures contain three types of peptides; those that i) have no affinity to any protein, ii) bind to a large number of proteins, or iii) show affinity to a specific protein. The later group may be further subdivided according to binding affinity and the specific site on the protein surface to which the peptide binds. It is necessary in a "screening" system to differentiate between these various peptides.

It has been noted above that protein also referred to herein as the target (R)/ligand (L) association may be described by the formula $$[R]+[L] \rightarrow [RL] \qquad (A)$$

and the equation $$K_b = k_1/k_2 = [RL]/[R][L] \qquad (1)$$

where $K_b$ is the binding constant and the rate constants $k_1$ and $k_2$ represent the forward and reverse rate constants, respectively. The general way in which peptides from synthetic libraries are screened is i) to use an excess of peptide, ii) control the conditions of association, iii) allow the system to come to equilibrium, and iv) then rapidly separate the unbound peptides from the RL complex. From this point on the various screening systems diverge in the identification of bound peptides.

The claimed approach is quite different than that used by others. The methods described herein allow us to select on the basis of the forward rate constant of a ligand for the receptor, the reverse (off) rate constant, or the equilibrium constant under conditions where it is possible to vary ionic strength, pH, concentration of competitive binding agents, organic solvent concentration, and temperature to name a few. All of these conditions potentially impact complex (RL) formation.

Selection of peptides based on their binding constant can be achieved in several different ways. One is through the use of a chromatography column with the receptor (R) immobilized. Another is in a chromatographic system in which the components of the RL complex are separated as the complex dissociates.

In the immobilized receptor approach, the receptor (R) is immobilized on a chromatography column. Since the association of ligand with immobilized receptor is biospecific, the affinity of that association is dictated by the equilibrium as show in eqn. 1 above. The equilibrium constant ($K_b$) may be related to the chromatographic behavior (k') by the equation $$K_b[R]=[RL]/[L]=K_d=k'/\theta \qquad (2)$$

Where $K_d$ is the chromatographic distribution coefficient and $\theta$ is the phase ratio. Rearranging the equations above it may be shown that $$k'=K_b[R]/\theta \qquad (3)$$

When receptor concentration [R] is large relative to [RL], then [R] may be assumed to be constant. Because the phase ratio ($\theta$) is also a constant, k' in the isocratic elution mode is directly proportional to the binding constant $K_b$.

The impact of band spreading on the screening process must also be considered. Estimation of band spreading is generally related to theoretical plates (N) in which $$N=16(V_e/v)^2 \qquad (4)$$

where $V_e$ is the elution volume of the analyte either in ml/min or column volumes (CV) and v is the peak width in the same volume units. At medium to high mobile phase velocity it is probable that columns will have 100 plates or less and plate heights will be 2 mm or more. This would mean that $$V_e=2.5v \qquad (5)$$

It may be concluded from these equations, that peaks will be very broad and it will be difficult to determine the peak maximum, i.e. k'. Furthermore, the resolution equation $$R_s(V_{e2}-V_{e1})/V \qquad (6)$$

shows that when v=0.4 $V_{e2}$, as would be the case in a 100 plate column.

Thus, when peaks are very broad, detection sensitivity is seriously compromised and it is difficult to determine k' as noted above. One solution is to collect and concentrate fractions of ligand eluting from the affinity column over a fixed time period and determine ligand concentration in the accumulated fraction. This may be achieved by using a reversed-phase chromatography column as an accumulator by coupling it in tandem with the affinity column. To determine k' by this method, multiple samples must be collected and quantitated to allow reconstruction of the chromatography peak. Assuming that the peak will always be of the same shape, k' may be estimated by determining the peak width and the fractional amount of the analyte eluted at any point in time.

The chromatography column is essentially one theoretical plate, i.e. 1–10 mm length, which is saturated with ligand (L) to form RL complex. Although substantial quantities of RL my be formed in the loading process, it is still possible that there is a finite quantity of residual receptor (R), especially as ligand elutes from the column. Elution of ligand (L) from this column depends on the dissociation process (formula B) in which $$[RL] \rightarrow [R] + [L] \quad (B)$$

Free ligand is swept from the system before it has the chance to recomplex with R to form RL. Because the binding constant is very large, i.e. >$10^6$, most of the ligand exists in the column in RL complex. This means that the rate of elution of ligand from the column will be described by the equation $$d[RL]/dt = -F[L]/V_c \quad (7)$$

where F is the volumetric flow rate (ml/min), [L] is ligand concentration, and $V_c$ is the column volume (ml). Integration indicates that $$\log [RL] = \{[L]F/V_c\} \log 1/t \quad (8)$$

But we know that $$K_b \{[RL]_i - [L]\}/\{[R]_i + [L]\}[L] \quad (9)$$

where $K_b$ is the binding constant, $[RL]_i$ is the initial concentration of the RL complex, and $[R]_i$ is the initial concentration of fee receptor. Substituting for [L] in the integrated form of the equation allows one to predict the rate of elution of ligand from the column as a function of the binding constant.

One may computer model the system in an iterative process in which a new equilibrium is computed each time one column volume saturated with ligand is swept from the column. In so doing it is assumed that the system is in equilibrium at all times and there are no significant mass transfer limitations.

Using binding constants that vary by orders of magnitude it can be shown that there is a strong selection for species with large binding constants to stay bound to the column while species with smaller binding constants are eluted.

When i) a mixture of ligands ($L_1, L_2, L_3 - - - L_n$) having binding constants for a receptor (R) exceeding $10^6$ are brought in contact with immobilized (R) and ii) the sum of the concentration of these ligands exceeds that of the receptor, the receptor will be saturated. Furthermore, when this system is allowed to come to equilibrium the relative concentration of the various species will be represented by the equation $$Kb_1[L_1]/[RL_1] = Kb_2[L_2]/[RL_2] = Kb_3[L_3]/[RL_3] = Kb_n[L_n]/[RL_n] \quad (9a)$$

Because the initial concentration of the various ligands is unknown, it is not possible to estimate binding constants on either a relative or absolute basis.

This is known as the equilibrium shift method. The equilibrium shift method is based on the following protocol. First an immobilized receptor column located on one of the valves of a multivaled liquid chromatograph is saturated with ligand(s) and the adsorbed ligands subsequently desorbed from the immobilized ligand column and reconcentrated on a reversed phase column through valve switching that couples the receptor and reversed phase columns in tandem. The receptor column is then switched out of the system and the ligands separated by gradient elution from the reversed phase column and quantitated.

Second, the immobilized receptor is again saturated with the ligand mixture. Free ligands are then rapidly eluted from the system with a 1.5 column volume wash that is discarded to waste. The receptor column is then switched into a fluidic loop in which liquid is pumped from a reservoir of volume (V') through a high pressure pump into the receptor column and then back into the reservoir. The volume of the pump, connecting tubing, and receptor column is V". The liquid volume (V) of the system is the sum of V'+V" Receptor:ligand complex [RL] will dissociate until the system once again comes to equilibrium as described by equation 1 above.

Let us consider a chromatography column of surface area As, saturated with ligand in which receptor density is [R], the density of complex (RL) is equal to [R]=[RL], and the amount of ligand adsorbed to the column is [RL]$_i$As. In the special case where 50% of the ligand initially adsorbed on the column desorbs from the surface and enters the liquid phase, i.e.

$$[RL]As = [L]V = \frac{1}{2}[RL]_iAs = [R]As \quad (10)$$

then $$K_b[L]V = 1 \quad (11)$$

In the more general case $$K_b\{a/(1-a)\}[L]V = 1 = (K_b\{a/(1-a)\}[RL]V)/2 \quad (12)$$

where a is the fraction of the initial adsorbed ligand that dissociates and enters the liquid phase and (1-a) is the fraction of the initial RL complex remaining after reequilibration. When two substances are bound $$K_{b1}\{a_1/(1-a_1)\}[RL_1]V = 1 = K_{b2}\{a_2/(1-a_2)\}[RL_2]V = 1 \quad (13)$$

to the column and $K_{b2}$ is the known, the equation $$K_{b1} = K_{b2}\{a_2/(1-a_2)\}[RL_2]\{(1-a_1)/a_1\}(1/[RL_1]) \quad (14)$$

allows one to calculate the binding constant $K_{b1}$ based on the relative amounts of the two substances eluted from the column when the equilibrium shifts to compensate for the increase in volume (V).

As noted above, screening may also be achieved in a chromatographic system by chromatographing the RL complex and separating receptor (R) from ligand (L) as the complex RL dissociates to prevent reassociation. In this process, RL complex of those ligands with the highest binding affinity will be the most likely to survive passage through the chromatographic system without dissociation. The rate at which R is separated from L, i.e. resolution ($R_s$) as a function of time ($dR_s/dt$), is an important issue. Resolution in a chromatographic system is shown in eqn. 6, where $R_s = (V_{e2} - V_{e1})/v$. Because dt is inversely related to mobile phase velocity ($V_m$), $$dR_s/dt = V_m(V_{e2} - V_{e1})/v \quad (15)$$

When elution volumes are converted to capacity factor and peak width expressed in terms of plate height and column length, equation 15 becomes $$dR_s/dt = [(k'_2 - k'_1)V_m(LH)^{1/2}]/4(k'_2 + 1) \quad (16)$$

In the case of size exclusion chromatography (SEC), when both R and RL are excluded from the pores $k'_1 = 0$ and eqn. 16 reduces to $$dR_s/dt = [k'_2 V_m(LH)^{1/2}]/4(k'_2 + 1) \quad (17)$$

Because peptides are small they will generally elute from an SEC column in the totally included volume, i.e. $V_0+V_i$. This means that $$K'_2 = V_i/V_0 \quad (18)$$

In this special case eqn. 18 becomes $$dR_s/dt = [(V_i/V_0)V_m(LH)^{1/2}]/[4\{(V_i/V_0)+1\}] \quad (19)$$

The case of size exclusion chromatography (SEC) is very similar to a dialysis system in which the inability of a macromolecular receptor to penetrate a pore matrix excludes it from certain liquid elements of the system. In the SEC system the RL complex dissociates and ligand (L) diffuses into the pores of the SEC matrix from which RL and R are excluded. Because the macromolecular R receptor moves through an SEC column faster than the low molecular weight ligand (L), R moves away from the zone of L in the pores of the support. This precludes reassociation to for RL. When this separation of R and L has occurred, more RL must dissociate to maintain the equilibrium in eqn. 1. When this separation of R and L occurs very rapidly, maintaining the equilibrium will become dependent on the off-rate ($k_2$). This means that a low mobile phase velocity selection will depend on the equilibrium constant ($K_b$) while at high mobile phase velocity selection will be based on the rate constant $k_2$.

Screening based on the rate of dissociation of the RL complex may be achieved in several ways as described above. In the systems described above, the concentration of receptor [R] increases as ligand elutes from a section of the column. Because the rate of complex formation is much higher than the rate of dissociation, it is impossible to carry out off-rate selection in porous chromatography sorbents. The concept described below allows off-rate selection by exploiting the fact that subsequent to complex dissociation there is a low probability that ligand will contact a receptor bearing surface again before elution from the system.

Mass transfer to the walls of open tubular columns eluted with aqueous mobile phases is known to be poor. Mass transfer to the walls of open tubular columns decreases with the inverse square of increasing column diameter and the square of increasing linear velocity of the mobile phase. Columns of 300–1000 μm with immobilized receptor (R) are loaded by filling the column with a series of ligands and allowing the system to come to equilibrium at zero mobile phase velocity. When the sum of the concentration of ligand species ($[L_1]$ - - - $[L_n]$)>[R], there is competition between the ligands for a binding site. The amount of any RL complex formed is a function of both the constant of the particular ligand for the receptor and the concentration of that ligand. After equilibrium has been achieved, unbound ligands are swept from the column. Elution of L in bound RL complex is based on the off-rate. Assuming that subsequent to dissociation of RL to L there is no reassociation, the rate of ligand (L) elution from the column is given by the equation $$-d[RL]/dt = k_2[RL] \quad (20)$$

where $k_2$ is the off-rate constant. Integrating between the limit of the initial concentration $[RL]_i$ of complex and the concentration [RL] at time t produces the equation $$2.3 \log([RL]/[RL]_i) = -k_2 t \quad (21)$$

The off-rate and the rate at which ligand are eluted from the column may also be expressed in terms of the half-life ($t_{1/2}$), i.e. the time it takes for half the ligand to elute from the column. From the equation above it may be shown that $$t_{1/2} = 0.693/k_2 \quad (22)$$

In summary, the basic assumption in this model of off-rate selection is that there will be no reassociation of R and L at the walls of the capillary once dissociation has occurred. This probably is not strictly true. The walls of a capillary are not well swept, i.e. there is a stagnant layer of liquid at the walls. L must diffuse through this layer before it escapes into the rapidly moving liquid in the center of the capillary where it is rapidly transported out of the capillary. The validity of using this model is that mass transfer i) dominates selection processes in chromatography columns and ii) it is orders of magnitude poorer in large open tubular capillaries than porous particles.

A family of chromatography columns have been developed over the past decade based on the concept that liquid chromatographic separations may be achieved i) through the use of porous matrices in which access of analytes to the interior of a particle is controlled by molecular size and ii) the chromatographic stationary phase is only on the inside of the particle. These "restricted access media, have been particularly useful in the separation of low molecular weight drugs in serum from proteins. The first of these columns was the "internal surface reversed phase" (ISRP) media. Another RAM type phase is the "semipermeable surface, "media".

These columns, as they apply to screening, may be thought of in the following—way. Because large receptor molecules would be excluded from access to the interior of ISRP media, they may be thought of as being similar to a dialysis membrane. In a dialysis system, the macromolecular receptor is restricted to one side of the membrane because it is excluded from passage through the pore network of the membrane by it's physical size. In contrast, small ligands may penetrate the pores of the membrane and gain access to all the liquid space within the system. Dialysis is achieved by repeatedly removing liquid containing ligand from the non-protein containing side of the membrane.

The ISRP chromatography system functions in screening by i) allowing only ligand (L) to gain access to the interior of particles which contain stationary phase, ii) capturing L with high affinity on the internal reversed phase when the RL complex dissociates and L diffuses into the interior of the ISRP containing particle, and iii) transporting RL complex through the chromatography column. This system will be vastly superior to the dialysis system based on the fact that i) it actively captures the low molecular weight species (L) being removed from the protein and ii) the stripping process is repeated many more times in the chromatography column than is practical in a dialysis system.

Still another characteristic of the ISRP approach is that diffusion distances to the surface of the particle, where L is captured, are small and L will be quickly captured following dissociation from the RL complex. This means that the rate of removing L will be dependent on the rate of dissociation, not the equilibrium constant $K_b$, it will also be possible to select from mixtures of many RL species.

B. Configurations

In certain embodiments, the invention may comprise a first column having the target of interest immobilized thereon. Thus, when the sample is passed over the first column, ligands which bind to the target will be immobilized thereon by forming a target/ligand complex. The complex captured by the first column is dissociated by varying the wash volumes.

The claimed invention provides a method, system and apparatus for obtaining information about a particular ligand without the need for manual manipulations, regardless of the size of the sample, or the amount of ligand present in the sample. These methods remarkably provide for the first time, rapid, automatable means for drug discovery. Literally millions of compounds can be screened for a particular biological activity in a short period of time, thus leading to significant advances in the field of biotechnology, pharmaceutical development, diagnostics and therapeutics. The methods of the invention allow the artisan to select ligands to a target of interest based upon any one or more characteristics, such as (1) the forward rate constant of a ligand for the target, i.e. on rate, (2) the reverse rate constant, i.e., off-rate, or the equilibrium constant under conditions where it is possible to vary ionic strength, pH, concentration of competitive binding agents, organic solvent concentration, and temperature, for example. Any conditions which may potentially impact the formation of a target/ligand complex may be varied and used as a selection criteria. The methods of the invention also allow the rapid selection of a ligand to a target of interest, characterization of virtually any potential binding characteristics of the ligand, and recovery of the ligand.

The methods of the invention use a tandem column chromatographic technique: any column capable of separating molecules can be used in the methods of the invention. Thus, depending on the result sought, the columns in the system may be chosen from the group consisting of affinity columns, size exclusion columns, and/or reversed phase columns. As used herein, the term "tandem mode" indicates that at least two columns are involved in the system, either simultaneously, or sequentially. If the columns are run simultaneously in tandem mode, then sample solution may be split and delivered to each column. If they are run sequentially, the columns are arranged so that the eluate of one column is directly introduced into the second column.

The claimed methods in various embodiments, may employ an affinity based column. In an affinity based screen, tandem-chromatographic columns are used to screen for ligands in a sample.

Reference will now be made in detail to the presently preferred embodiments of the invention. The multi-dimensional methods of the invention in various embodiments relate to detecting the presence of a ligand having an affinity K for a preselected target molecule in a sample of heterogeneous ligands dissolved in a solvent. The invention contemplates both the methods themselves, as well as multi-dimensional systems or methods including one or more dimensions. In various claims, the invention relates specifically to various dimension embodiments which are novel. The invention allows one to recover target-bound ligands, as well as simultaneously select ligands and determine their relative affinities during the screening process. As embodied herein, the invention relates to a multi-dimensional method, apparatus and system for the highly sensitive detection and analysis of ligands or analytes in samples, and to assays and other "dimensions" of the system. The invention comprises a multi-dimensional system which may include, for example, the screening of libraries, selection of ligands, and recovery and ligands with a desired activity, and subsequent identification. More specifically, dimensions may include any method of partitioning components of a sample, including, for example, immunoassays, such as affinity chromatography, reversed phase chromatography, and size exclusion chromatography. The techniques described in the specification and claims herein provide a multidimensional approach to screening samples, in which separations, chemical reactions, and mass spectrometry are integrated, and, preferably, automated.

The multi-dimensional system and methods may, in various embodiments include the following steps: (1) generation of a sample of potential ligands; (2) providing a support with a concentration of a target molecule immobilized thereon; (3) screening for a ligand to the target molecule, wherein the ligand has one or more desired properties; (4) separation of those ligands desired; (5) recovery of the ligand obtained; (6) identification of the selected ligands; and (7) large scale synthesis of the ligand or derivatives thereof for diagnostic or therapeutic applications. The most effective combination of analysis dimensions can easily be determined by one skilled in the art based upon the particular results desired.

Such multidimensional systems allow the rapid screening of libraries of ligands for their ability to bind to a certain "target molecule" ("target" or "receptor") of interest. The target molecule can be any molecule to which a ligand is desired, such as, for example, proteins, peptides, nucleic acids, monoclonal or polyclonal antibodies, etc.

Screening soluble libraries of peptides or small molecules for identification of ligands binding to a specific target molecule has become a widely used technique in the pharmaceutical industry. Screening these libraries may lead to development of novel therapeutics and/or diagnostics. Screening requires both a selection process and a method to assess the relative affinities of the ligands. Methods known in the art thus require two separate steps to determine the acceptability of a particular ligand. Often, after screening the sample and recovering a desired ligand, it is discovered that the ligand selected has an undesirable affinity for the ligand. As will be recognized by one skilled in the art, different applications often require ligands having a specific affinity. Numerous variables must be taken into account to determine the applicability of the selected ligand for the desired application. For example, one may prefer a ligand having a particular on or off rate, or a ligand which binds to one target molecule, but not another. Until the present invention, therefore, the entire selection process involved several separate steps, in order to not only identify a ligand to a target, but to further select based upon additional characteristics.

The claimed methods allow the novel and rapid determination of relative affinities for ligands which bind to a selected target molecule, additionally, the methods provide for the recovery of the target-bound ligands, and offers the simultaneous selection of ligands and determination of their relative affinities or other binding characteristics during the screening of a library of compounds Multi-dimensional analysis systems as disclosed and claimed herein provide multiple embodiments suitable for the screening, selection and recovery of desired ligands. It is preferable to automate these assays, however, solvent compatibility has historically been a significant drawback to this approach. The inventors have avoided this problem by incorporating a universal solvent exchange method into their multi-dimensional assay systems.

In various embodiments, the invention relates to multi-dimensional separations which provide for the high resolution of complex mixtures. Because of the ability to directly couple various analytical components, sample handling and transfer steps can be virtually eliminated. This is especially critical when one is attempting to isolate and detect ligands present at very low detection levels.

The claimed system contemplates a multi-dimensional system which may incorporate a series of chromatography columns such as size-exclusion, ion exchange and reverse phase, as well as one or more detectors, such as a mass spectrometer.

The integrated coupling of various dimensions such as micro column affinity chromatography with capillary reverse phase HPLC/electrospray ionization mass spectrometry in an automated multidimensional system should permit a highly sensitive and highly selective approach to decoding complex mixtures. The system should allow for rapid column and solvent switching capabilities. One skilled in the art can easily add extra dimensions to the system by subjecting the sample, or a subset thereof, to more separation or identification processes. Any suitable "dimension" may be added to the system, i.e. any separation processes such as two different chromatographic columns, or any other separation processes, that produce different spatial or temporal distributions of the individual components of the system.

The claimed invention encompasses a multi-dimensional system comprising two or more chromatographic or other separation dimensions which are plumbed in tandem mode. In a basic embodiment, two chromatography columns are plumbed in tandem mode. The first column is selected based upon the desired application and the basis of the sample. The first column may be an affinity chromatography, i.e. a column containing a stationary porous medium that has a different affinity for the various components in the sample; however, one may also use a non-porous medium. This column can be any solid support having immobilized thereon the target of interest. Such preselected targets may be molecules such as receptors, enzymes, nucleic acids, polysaccharides, mucopolysaccharides, antibodies or binding proteins. Additionally useful target molecules include major histocompatibility molecules, T-cell receptors, antigens, cell-adhesion molecules, cellular receptors for hormones and growth regulatory factors and virus receptors. Ligands to these targets of interest provide a collection of possible immune agonists, antagonists, antiviral ligands and structural lead compounds for the design of small molecules with a desired bioactivity. As the sample solution passes through the support, ligands to the target will adsorb at the binding sites, and be retained on the column. A certain amount of solution components may also non-specifically bind to the support.

The affinity columns to be used in the invention may comprise any solid support which does not affect the binding activity of the target molecule. Supports commonly utilized are controlled pore glass, silica, silica gel, membranes, polystyrene based beaded supports, glass fibre frits and paper filters. While perfusive matrix materials are preferred, the invention also can be practiced with a non-porous matrix, in which tortuous channels are formed by the interstitial space among non-porous packed particles. These matrices have a lower net capacity than perfusive matrices but they may be very useful for microanalysis. In addition to packed particles, matrices useful in the process and apparatus of the invention may be embodied as bundles of microcapillaries. A high surface area/volume ratio may be provided by the use of very small internal diameter capillaries, providing a reaction vessel of a few microliters/cm. Likewise, the binding protein may be coated on the inner surface of the capillary tube. Solutes may be transported through the capillary tube matrix by convection. The high surface area to volume ratio of the capillary tubes increases the available reaction volume. The matrices may further comprise a membrane structure.

The matrix preferably is a rigid substantially non-microporous, particulate material having a hydrophilic surface, and preferably is also a perfusive chromatography matrix. The matrix also may be defined by the interior surface of a capillary. The methods comprise first loading a column with a known concentration T of target molecules.

In an alternative embodiment, the first column may comprise a size-exclusion column or dialysis system, capable of separating components of the sample based on size. The different components of the sample will migrate through the column at different rates; ligands which have bound to the target, thereby forming a complex will elute prior to the elution of smaller molecular species. Thus, the first portion of the exiting stream will contain the ligand bound to the target. It is preferable to use particles capable of perfusion chromatography since perfusion particles allow the system to operate at very high flow rates while maintaining both high sample loading capacity and chromatographic resolution. Preferably, the perfusion particles are POROS™ beads available from PerSeptive Biosystems Inc. (Framingham, Mass.).

In various embodiments of the invention, a second column, plumbed in tandem mode with the first is yet another chromatography separation column. Specifically, the second column may be an affinity column, as described above, having immobilized thereon a second target of interest having different physicochemical properties than the target immobilized on the first column. This configuration will enable one to select and separate ligands based upon one or more different phsyico-chemical properties. It may also be envisioned that both the first and second column have immobilized thereon the same target of interest, as a confirmation assay.

Alternatively, the second column may be an accumulator, i.e. a column designed to non-specifically adsorb ligands and optionally, to permit the separation of the adsorbed ligands by elution. A reversed phase column is a preferable accumulator.

Increasing the wash volumes will result in the highest affinity ligands being retained on the column for the longest period of time. Low affinity ligands, conversely, will have a shorter retention time on the column. There is a direct correlation between the wash volumes employed to wash ligands bound to the first column and their relative affinities.

In various embodiments, the wash volumes passed over the first column are indicative of the dissociation rate from the target. For example, if various ligands are passed over the first column and incubated to equilibrium, the presence of a particular ligand in the eluate must be a factor of the dissociation rate from the target. The dissociation rate is dependent on time, dilution, and association/dissociation rate constants. The time and dilution factors may be controlled, and thus, the loss of ligand bound to its target under these conditions should be directly related to the dissociation rate constant (i.e. off-rate) of the ligand. The target molecule may be preequilibrated with a ligand prior to immobilization, or prior to introduction of the soluble library.

Thus, in certain embodiments, the first affinity column having a target immobilized thereon, is plumbed, in tandem mode, to an accumulator, such as a reversed phase column to immobilize thereon ligands having the desired affinity.

The elution of the reversed-phase column allows recovery of the ligands, and the peak heights of corresponding peaks provide a measurement of the amount of the ligand bound to the target at a specific wash volume. Under these conditions, the wash volume correlates with the dissociation rate constants of the ligands, and may provide an indication of relative affinities of the ligands having a similar mode of interaction with a target. The methods can be applied to the screening of a library of compounds where selection of ligands and determination of their relative affinities can be accomplished simultaneously, enabling selection of binders with the desired affinity.

Thus, for the first time, the practitioner is able to select a ligand based not only on its ability to bind to a target, but also upon its affinity for that target, i.e. the on-rate or dissociation rate (off-rate). This ability is especially relevant in drug screening applications where the dissociation rate may be critical to the effectiveness of the composition. Since the ligands bound to the target can be later recovered, further characterization or development of the selected binders can be performed, as discussed in more detail below.

The methods allow the practitioner to select ligands to the target of interest using virtually any affinity selection method. For example, by varying the stringency, i.e. varying the wash volumes, one can to select based upon for example (1) affinity, (2) on rate or off rate; (3) the wash conditions (pH, ionic strength, temperature).

The methods allow the practitioner to select ligands to the target of interest using virtually any affinity selection method. The most effective combination of analysis dimensions can easily be determined by one skilled in the art based upon the particular results desired. The claimed system is advantageous in that the direct coupling of various unit operations with $\mu$L volume connections diminishes the dilution, loss and contamination of samples by circumventing fraction collection and manual sample transfers. A second advantage is the use of direct transfer with analyte enrichment at the inlet of down-stream columns either directly or through the use of mobile phase exchange systems. For example, an accumulator, such as a reversed phase column may be positioned between any dimensions of the system. This eliminates the manual operations of concentrating and exchanging mobile phases between separations steps.

Additionally, the methods described above can be configured so as to characterize the interaction between different ligands. These experiments can be conveniently performed by plumbing various columns in tandem mode, and without a need for attaching a label to the ligand. One or more of factors can be combined to achieve the desired result.

Thus, in certain embodiments, the practitioner can use the methods of the invention to screen ligands for their ability to bind to a certain first target molecule, and their inability to bind to a second target. This technique should be generally applicable for selecting ligands that differentiate between two different targets. The claimed methods remarkably allow the artisan to rapidly select ligands based upon their ability to bind to certain targets, and not others. This ability is especially critical in the pharmaceutical field, where potential new drugs may interfere not only with foreign or pathogenic targets, but also with host molecules. This is due to the highly conservative nature of the pathogenic and host targets. Using the claimed methods, a ligand can be selected that binds, for example, to a pathogenic target, i.e. a bacterial protein, but not to the homologous host target. This technique, referred to as subtractive screening, can be used to differentiate between any two binding characteristics. For example, the technique not only can differentiate between pathogens and hosts, but can also be used to differentiate between, a chiral or non-chiral form of a molecule; wild type target versus mutant proteins and various subclasses or variants of a target.

Alternatively, one can immobilize one subclass on a column, and introduce both the sample solution and the second subclass target molecule. The ligands which preferentially bind to the second subclass target spend more time in the mobile phase, and thus are eluted first from the column. Ligands which preferentially bind to the first subclass target will be the last to elute from the column. Obviously, the middle eluate is a combination of varying affinities for both subclass one and two.

In other embodiments, the methods and systems of the invention encompass other techniques for selecting ligands to a target of interest. The inventors have developed a novel methods not only for selecting particular ligands based on affinity or subtractive screening, but also for selecting ligands which bind to a target of interest at a particular binding site. In the latter embodiments, the invention contemplates the use of a first separation system, followed by an accumulator such as a reversed phase column. As discussed above, the methods involve two dimensions, plumbed in tandem mode.

The first dimension, a size exclusion chromatography system, is very similar to a dialysis system in which the inability of a target or receptor to penetrate a pore matrix excludes it from certain liquid elements of the system. In fact, this first dimension can be a dialysis system or any other system capable of separating target/ligand complexes and unbound components. Thus, one may contact a sample solution with the target of interest, ligands to the target will bind thereto. The solution may then contain a mixture of unbound sample components and ligand/target complex which may be introduced into an SEC column. Alternatively, one may introduce the target and sample directly into the SEC column. When one introduces this mixture to an SEC system, unbound components will diffuse into the pores of the SEC matrix, however the complex, and the target are excluded because of their size. Because the macromolecular target/ligand complex moves through an SEC column faster than the lower molecular weight components, the complex will elute from the column first. The eluate containing target/ligand complexes can then be introduced to a second dimension such as an affinity column. One immobilizes a known ligand to the binding site of interest on the affinity column. Ligands which elute off this second column will be those ligands which bind at the site of interest which were displaced by the known ligand immobilized to the column. When the eluate passes through the immobilized column Weakly bound complexes may dissociate when the separation of target and ligand occurs very rapidly, maintaining the equilibrium will become dependent on the off-rate ($k_2$). This means that a low mobile phase velocity selection will depend on the equilibrium constant while at high mobile phase velocity the selection will be based on the rate constant $k_2$.

Thus, one may select for a ligand which will interfere with the binding activity of the natural ligand/target pair. Ligands identified by this technique are particularly well suited for use as pharmaceuticals or diagnostic aids. For example, scientists have recognized the relationship between CD4 and GP120, in those infected with the human immunodeficiency virus (HIV). Thus, it would be beneficial to obtain a ligand which can disrupt the interaction between these two molecules, thereby inactivating the active complex. Using an affinity column, one can select ligands which bind to the target of interest. Those ligands which do bind are eluted from the affinity column and introduced into another affinity column. The second column may be a size exclusion column. The eluted target/ligand complexes from the first column are then introduced to the second column, along with a known ligand. The known ligand can be any ligand known to bind at the particular epitope one is seeking a binder to. Thus, the known ligand will compete with the ligand on the target/ligand complex, and displace ligands which bind at the selected site on the target molecule.

One can envision applications of this technique wherein a DNA transcription factor is immobilized on the second column thereby facilitating the detection of a ligand which binds at the same site on the transcription factor as DNA.

Alternative techniques of obtaining the same result exist using the claimed methods. For example, to select site specific binders, one can compare the eluate from a column containing both the target molecule and a known ligand with eluate from a column containing only target molecule.

Screening based on the rate of dissociation of the ligand/target complex may be achieved in several ways. In the systems described above, the concentration of the target increases as the ligand elutes from a section of the column. Because the rate of complex formation is much higher than the rate of dissociation, it is impossible to carry out the off-rate selection in porous chromatography sorbents. The embodiment described below allows off-rate selection by exploiting the fact that, subsequent to complex dissociation, there is a low probability that the ligand will contact a target bearing surface again before elution from the system.

In various embodiments, additional dimensions relate to selecting and recovering ligands with a preselected affinity for a target of interest preselected affinity refers to the ability of the ligand to specifically bind to the target molecule, i.e. the strength of the interaction between target and ligand. Typical values for the preselected affinity are in the order of $10^{-3}$ l/mol to about $10^{-4}$ l/mol at a minimum, and are preferably about $10^{-8}$ to about $10^{-10}$ l/mole. The preselected affinity value is dependent on the environment in which the ligand and target molecule are found, as well as their concentration. Preferably K is an affinity between about 10.5 M-1 to 1-0.16 M-1.

In some applications, a lower affinity is acceptable, while in other applications, the affinity value may be much higher. One skilled in the art can routinely determine the desired affinity constant depending on the particular target and application of interest.

It is also possible to select specific binding conditions through the selection of the mobile phase with which the column is washed subsequent to peptide binding. To determine T for a particular application, one skilled in the art can calibrate an affinity column using any of the methods known in the art. For example, one may calibrate the column by introducing a pure sample of a ligand having a known affinity constant for binding to the immobilized target. The ligand is then loaded onto the column. Serial column volumes are then passed through the column, and directly introduced into the accumulator, until one obtains the ligand with the known affinity constant K'. T can then be calculated based upon the following equation:

$$T = \frac{K'}{K_{(known)}}$$

Thus, K', also known as the retention factor is defined by the equation $$K' = K \times (T)$$

In practice, therefore, if one desired to obtain a ligand having an affinity constant K of $10^{10}$, T could be set at, for example, $10^{-8}$ M. The ligand having the preselected affinity K will be obtained upon passing approximately 100 column volumes of solvent through the column.

$$10^{10} = \frac{K'}{10^{-8}}$$

After the sample is passed through the column so that ligands bind to the target molecules, a series column volumes of solvent are passed through the column, wherein n is a number of column volumes between 1 and 10,000. A subset kp of the volumes exiting the column are then passed to a ligand accumulator to immobile thereon ligands having the preselected affinity K. Elution of the affinity bound material is typically performed under conditions of high salt or acidic pH. Once eluted, the soluble sample can be analyzed to determine the presence or absence of the ligand to the target of interest, or to characterize a ligand to the target of interest. Analysis may be performed by any method suitable for the determination of components.

In yet other embodiments, the invention relates to a method, system and apparatus for separating ligands in a sample into groups having similar affinity constants. One skilled in the art can determine for each application the range of affinity constants to be included in each group depending upon the desired result.

In this embodiment, the artisan first selects which groups of affinity constants are desired. For example, if T is $10^{-5}$, and volumes 20–30 and volumes 500–800 have been collected from the accumulator, then the K for the ligands in each group can be determined as follows:
the presence $$K = \frac{2 \times 10^1}{10^{-5}} = 2 \times 10^6 \text{ and}$$

$$K = \frac{3 \times 10^1}{10^{-5}} = 3 \times 10^6$$

and the K for the 500–800 volumes will be between $$K = \frac{5 \times 10^2}{10^{-5}} = 5 \times 10^7 \text{ and}$$

$$K = \frac{8 \times 10^2}{10^{-5}} = 8 \times 10^7$$

Thus, in a basic embodiment, the methods, apparatus and system of the invention allow one to detect the presence of, or determine the affinity constant of biomolecules. Varying concentrations of ligands in a sample can be introduced to a column having a fixed concentration of target. The concentration of the unbound ligands varies with the initial target concentration, and following automated data manipulation, the affinity constant can be determined.

The screening procedure can be used repeatedly to detect ligands or analytes from these sample libraries, having a preselected affinity. One may prefer the binding constant gradient obtained for one ligand to the target of interest to that of another, depending upon the desired elution conditions. For example, the strength of binding in a series of solutions containing methanol at increasing concentrations or solutions with increasing salt concentrations simulating elution gradients can be used. In this way, one can evaluate the comparative behavior of a number of ligands at a multitude of elution conditions.

The target immobilized column may be directly coupled to an accumulator, such as a reverse phase column. The method in various embodiments employs a tandem column chromatographic technique in which the target-ligand complex captured by the first column is dissociated and eluted directly onto an accumulator such as a reverse phase column for caption of the dissociated ligands. The bound complex can then be dissociated from the column, and introduced into the RP column. The accumulator should be suitable for selecting the bound ligand-target complexes eluted from the chromatography column. If the accumulator is, for example, a size exclusion chromatography column, one can assume that the, if the flow rate through the SEC column is rapid, there is little time for the dissociation of the target-ligand complex. At a slow flow rate, the opposite is true. As discussed in greater detail above, there is a direct correlation between the amount of washing of the complex on the first column with the relative affinities of the ligands.

The methods of the invention also encompass the preparation of pharmaceutically active compositions wherein a ligand in a sample having a preselected affinity K for a target molecule of interest is identified. The ligand is identified by loading a column with a known concentration T of target molecules; passing a sample A through the column to bind ligands in the sample, and passing through the column a series of column volumes of solvent. A subset of the column volumes exiting the column are then passed to an accumulator to immobilize thereon ligands having the preselected affinity. The ligand is then eluted, and the ligand, or a derivative thereof is used to generate a biologically active component for incorporation into a pharmaceutical preparation. If desired, one may incorporate appropriate adjuvants therapeutic carrier, etc. A pharmaceutical preparation obtained by any of the above methods can provide a method of treatment by administration of the preparation.

The methods of the invention include methods for detecting a ligand having a desired high affinity K for a preselected target molecule when the ligand and the target molecule are present together in preselected solvent conditions. The ligand may be present in a heterogeneous sample comprising a multiplicity of ligand species. These methods comprise immobilizing a target molecule onto a column, passing the sample through the column under conditions to promote binding of ligands in the sample to the target molecules, and then passing through the column a series of column volumes of solvent defining the solvent conditions. One then passes a subset kp of the column volumes exiting the column through a ligand accumulator to immobilize ligands having the desired high affinity. The ligands are then eluted, and optionally, identified. The ligand obtained may be characterized by a high affinity K for the target molecule equal approximately to kp/T where T is the concentration of target molecules in the column. Optionally, the sample may be passed through the column to promote the binding of ligands under solvent conditions different from the preselected solvent conditions.

In other aspects of the invention, a ligand having a high on-rate, Ko, when the target molecule and the ligand are present together in preselected solvent conditions is detected. The ligand may be present in a heterogeneous sample comprising multiple ligand species, at least one of which binds a preselected target molecule with an affinity of at least about $10^4 M^{-1}$. As in other embodiments, the target molecule is immobilized on a column. A heterogeneous sample in a solvent defining preselected solvent conditions is provided, and; then passed through the column at a high linear fluid velocity so as to minimize the residence time of ligands in the sample. Thus, one selectively binds high on-rate ligands to the target molecules, in preference to other ligands in the sample. One then elutes the column to produce an output, and obtains or identifies the high on-rate ligand. One may optionally pass the output through a ligand accumulator, and then elute the accumulator to produce an output rich in the high on-rate ligand.

C. The Interfaces

The system and apparatus of the invention may also include a coupling interface for capturing the eluent from one dimension and introducing it to one or more different dimensions. The interface may optionally contain a buffer system to effectively desalt, dilute or remove organic solvent from the eluent of one dimension prior to loading in the next dimension. Thus, in some situations, one may incorporate a buffer exchange in the interface. The buffer exchange may be a mixed bed matrix, packed with cation and anion exchange sorbent. Alternatively, the buffer exchange may comprise a separate column for each of the cation and anion exchange sorbent.

Tandem columns of cation exchanger and anion exchanger, or a mixed bed exchanger can be used to capture biomolecules from the eluent of a column. Thus, for example, if one eluted a desired ligand from any column in the system with an acid, the eluant could be directed into a tandem buffer exchange to alter the pH prior to introduction to the next column. The eluant may first be introduced into a cation exchange column which will capture the ligands from the eluant. The cation column is then washed with a neutral pH buffer, and the desired ligands captured onto the subsequent column, i.e. an anion exchange column. The ligands can then be eluted off this second column with a buffer or solvent optimized for introduction into the next dimension of the system.

The buffer exchange interface is particularly valuable in multi-dimensional systems where the elution buffer of, for example, an affinity column, is not suitable for introduction into a mass spectrometer. Thus, the desired ligands are washed from the affinity column, passed through a cation column and an anion column prior to introduction into the mass spectrometer.

In an alternative embodiment, the claimed invention relates to the tandem use of an affinity column, and a column having immobilized thereon an enzyme for digestion. Thus, a desired ligand may be captured in the first column, an affinity column, and eluted with acid. The eluant may then be captured on a cation exchange column. The desired ligand can then be eluted of the cation exchange column with a buffer optimized for the next column, i.e. a trypsin column. Upon passing through the trypsin column, the ligand is digested and may, for example, be captured on a reversed phase column.

One can manipulate either the pH or salt to elute different columns; various configurations of the anion and cation columns are contemplated and can be configured so as to optimize the buffers for subsequent dimensions. It would be possible that this technology could be extended to quality control and process monitoring in biotech applications, the study of therapeutic protein and drug metabolism, and large scale screening programs of environmental and clinical importance.

Preferably the interface further comprises a multi-valving system capable of the direct transfer of solutes from one dimension to the next without dilution or manual intervention. The claimed invention may have both the buffer interface described above, and the valving interface, depending on the desired application.

Figure 2:
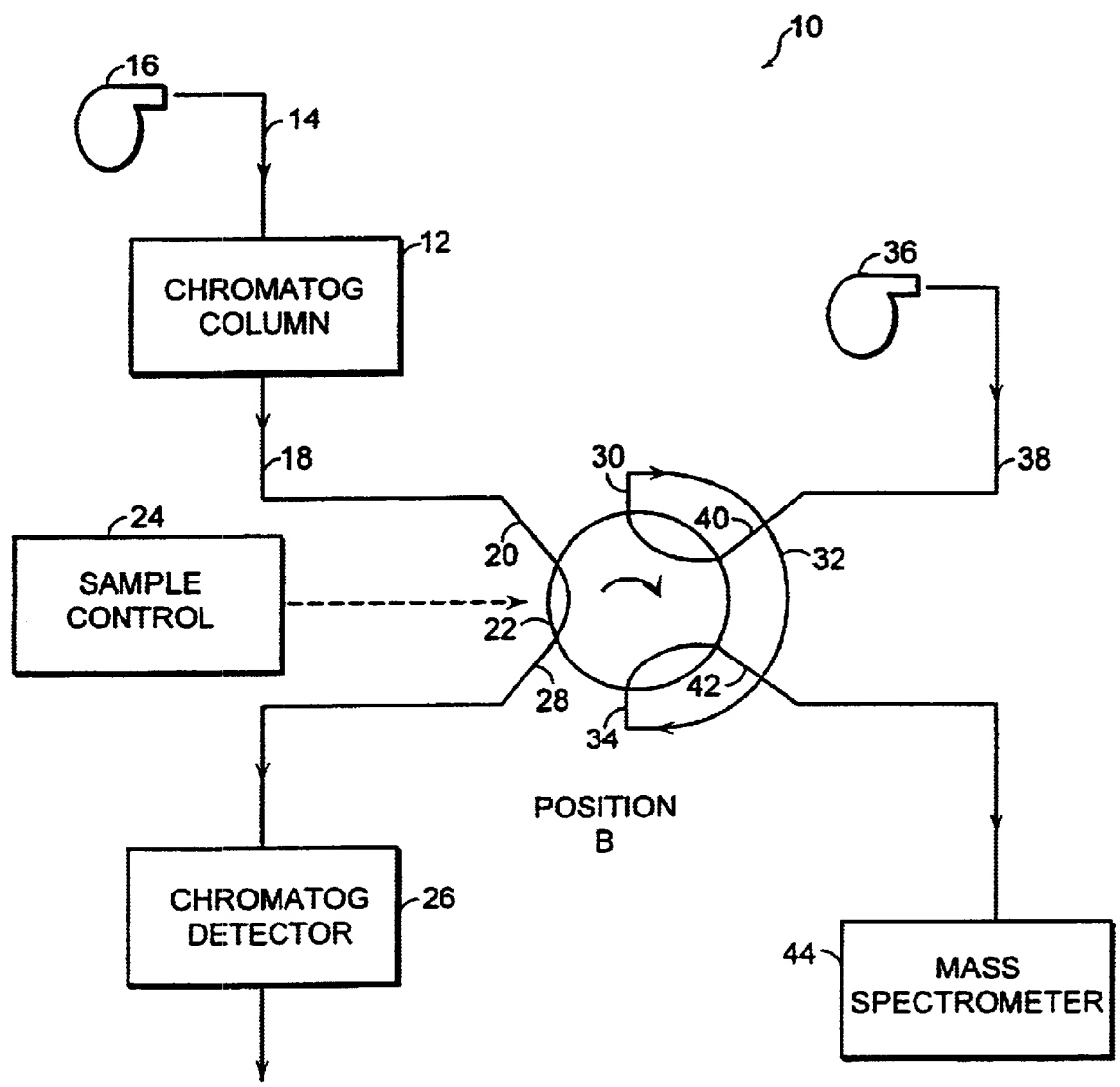
FIG. 2 is a schematic representation of a second embodiment of the apparatus of the invention.

The claimed invention encompasses a valving system which will avoid the laborious process of collecting solutes from each column and reintroducing them onto a second column. In several embodiments, the valving system is a "sample splitter" which allows a liquid chromatography eluent to be interfaced to a mass spectrometer (FIGS. 1 and 2). The advantage of the claimed interface is that the flow rate of the mass spec (MS) and the liquid chromatography column (LC) can be independent and variable, i.e., the MS and LC rates can be independently optimized while the MS sampling is decoupled from the LC flow rate. The invention also contemplates an interface capable of simultaneously sampling LC eluent from multiple LC columns and desalting an LC eluent sample prior to introducing the sample to the MS.

For example, the interface of the invention may be an interface for, i.e., sampling the eluent of a LC stream and injecting into another LC stream, or a detector such as a mass spectrometer. Thus, FIGS. 1 and 2 depict an embodiment of an analytical chemistry system 10, featuring a liquid chromatography/mass spectrometry sample splitter interface. The liquid chromatography column 12, having a liquid stream 14 driven at the desired rate for the liquid chromatography column by a pump 16, and a mass spectrometer 44 having a liquid analysis stream 38 driven at the desired rate for the mass spectrometer by a precision pump 36. A sampling valve 22 is cycled at a predetermined sampling rate to insert a sampling volume into the liquid chromatography stream to take a sample of the liquid chromatography eluent, and then into the mass spectrometer stream to analyze the sample.

More specifically, the liquid chromatography eluent 18 from the LC column 12 flows into an input port 20 of a sampling valve 22 and out through an output port determined by the selected position of the valve. An LC detector 26 can be connected to an output port 28 of the sampling valve 22 to accept the LC eluent from the LC column directed through the sample valve. Alternatively, the LC detector can be placed between the LC column and the input port 20 of sampling valve 22 with similar results.

Sampling valve 22 can, for example, be a rotary multi-port valve capable of two possible by-pass configurations and controlled by a sample controller 24. FIG. 1 shows the sampling valve in a first position A, and FIG. 2 shows the sampling valve in a second position B. In valve position A the LC stream sampling position, the eluant 18 from LC column 12 enters the sampling valve through input port 20 and exits the valve through output port 30. Output port 30 is connected to another input port 34 by a length of tubing 32 defining a sample loop having a predetermined sample volume. In position A, LC eluant flow through the sample volume into input port 34 and is directed to output port 28 for detection.

A MS precision pump 36 pumps MS analysis stream 38 into another sampling valve input port 40, and MS 44 accepts its analysis stream from another sampling valve output port 42. In valve position A, the MS stream 38 goes through input port 40 directly to output port 42 and to MS 44.

Upon switching the sampling valve 22 from position A to position B (FIG. 2), the MS infection position, the predetermined sample volume of LC eluant is trapped in the tubing 32, and transferred into the MS analysis stream 38. Specifically, in position B, sample valve 22 directs the LC eluant through input port 20 directly to output port 28 and to the LC detector 26. However, the MS analysis stream 38 is now directed through sample loop tubing 32 into MS 44, thereby injecting the trapped sample volume of LC eluant in tubing 32 into the MS analysis stream.

In operation, the flow rate of the stream for the LC column 12 can be substantially different than the flow rate of the analysis stream for the MS 44. For example, a typical LC flow rate can be greater than 100 µl/min. An MS flow rate can typically range form 1 to 10 µl/min. Furthermore, either the LC or the MS, or both flow rates can be dynamically variable.

Sample controller 24 operates to cycle the sample valve 22 to split the LC flow such that only a small portion of the flow from the LC eluant stream is injected into the MS analysis stream. The sample volume of the sample loop tubing 32 can be selected to have a negligible effect on the LC stream, yet be sufficient for the MS analysis. For example, a 1 µl sample volume removed from the LC stream would have a negligible effect on a 100 µl/min. LC stream, yet would be a sufficient sample for a 10 µl/min. MS stream.

When sampling valve 22 is cycled to position A, the LC eluant from the LC column 12 is caused to flow through sample loop tubing 32, filling the sample volume. Upon cycling sampling valve 22 from position A to position B, the sample volume of LC eluant trapped in the sample loop tubing 32 is pushed out of the loop to the MS at the MS flow rate of, for example, 1 to 10 µl/min. At an assumed MS analysis stream flow rate of 10 µl/min., 166 nl of the MS analysis stream are driven through the sample loop 32 sample volume every second. When the sampling valve is returned to position A, any residual sample left in the sample loop 32 is driven into the chromatography detector 26, fraction collector or waste, depending on the configuration of the system.

In operation, sampling valve 22 is cycled repeatedly to capture and transfer an aliquot of LC eluent to the MS analysis stream several times over each LC peak. By repeatedly sampling throughout the chromatographic peak of the sample, it is possible to reconstruct the chromatography from these discrete samples.

Depending on the desired application, the sample valving system may be configured to simultaneously monitor two or more liquid chromatography streams.

The multi-dimensional apparatus of the invention may also consist of an interface such as a fluid handling system with pumps for delivering the samples to the various dimensions, one or more chromatography columns and a mass spectrometer for detection. The system and apparatus of the invention may have a software interface, i.e. controller, which allows for a wide variety of assay formats, and may optionally include a spectrophotometric detector. The software interface may be tailored to a broad range of specifications and comprises three functional areas: instrumental control, methods development, and analysis. The instrument control may provide a graphical interface to each physical element of the system, from buffer selection to sample preparation, through to detection and fraction collection. The status of the system may be continuously monitored and displayed on the computer screen.

D. Detection

Any method of detection known in the art is suitable for use in the claimed invention. Thus, ligands, or target molecules may be labelled to render them detectable. Thus, either the target or the ligand may be labelled with a detectable moiety such as enzymes, fluorophores, chromophores, radioisotopes, electrochemical moieties and chemoluminescent moieties. Additionally, the invention contemplates a composition comprising a first binding partner having a detectable moiety which is intrinsic, e.g. a functional group capable of detection.

Additional methods of detection include, for example, any apparatus for obtaining mass-to-charge ratio, including, but not limited to: matrix-assisted laser desorption ionization/plasma desorption ionization, electrospray ionization, thermospray ionization, and fast atom bombardment ionization. Additionally, any mode of mass analysis is suitable for use with the instant invention, including but not limited to: time of flight, quadrapole, ion trap, and sector analysis. The preferred method of detection and analysis is an improved time of flight instrument which allows independent control of potential on sample and extraction elements, as described in copending U.S. Ser. No. 08/446,544 (Atty. Docket No. Syp-111, filed May 19, 1995).

The methods development component allows the user to create automated assay methods, including setup of injection sequences and sample preparation. Dilution and derivatization may be included in sample preparation.

Assay analysis allows the quantification of individual runs, and may incorporate parameters such as standard curves or dose levels to be prepared. Thus, a standard curve may be developed from a set of assays by automatically measuring the detector response and fitting this result to the injected sample quantity. This means that an entire set of assays, including standard curve generation, can be conducted with minimum operator intervention thus increasing the accuracy and decreasing the contamination of the assay.

The methods development component allows the user to create automated assay methods, including setup of injection sequences and sample preparation. Dilution and derivatization may be included in sample preparation.

Assay analysis allows the quantification of individual runs, and may incorporate parameters such as standard curves or dose levels to be prepared. Thus, a standard curve may be developed from a set of assays by automatically measuring the detector response and fitting this result to the injected sample quantity. This means that an entire set of assays, including standard curve generation, can be conducted with minimum operator intervention thus increasing the accuracy and decreasing the contamination of the assay.

It will be understood by those skilled in the art that the claimed invention contemplates not only detecting the presence of a ligand having a preselected affinity, but also recovery of that ligand, and its subsequent use. For example, ligands having a preselected specific affinity for a target toxin may be used as scavengers, in vivo and in vitro. The ligands thus obtained can be used therapeutically. Additionally, the methods, apparatus and system of the invention can be used to find lead compounds for drug discovery. The claimed invention relates not only to lead compounds, but also to the use of those lead compounds to identify new drugs. The invention also contemplates preparations prepared using the ligands of the invention.

The kits of the invention include apparatus capable of performing at least one "dimension" or method described above. It is preferable that the kits be capable, for example, of the automated detection of a ligand in a sample, having a preselected affinity K for a preselected target molecule. Such kits may contain a column having a known concentration of the preselected target molecule immobilized thereon, and an accumulator capable of receiving eluate from the column, and immobilizing thereon a ligand with the preselected affinity K. The kits may be adapted to any or all of the methods described above, and claimed herein.

The kits may optionally be configured to detect ligands as well as to analyze, and obtain said ligands, and may include, for example, an interface for rendering a sample solution compatible with additional analyses. The kits of the invention may be used to identify and obtain ligands in samples. The ligands, or derivatives or modifications thereof can be used for a variety of purposes, such as lead compounds for drug discovery. Optionally, one may use the ligands or modifications or derivatives thereof to prepare a pharmaceutically active composition.

Pharmaceutically active compositions of the invention are prepared by identifying ligands in samples having a preselected affinity K for a target molecule of interest. The ligand may be identified by loading a column with a known concentration T of target molecules, passing a sample through the column to bind ligands in the sample thereto, and then passing a series of column volumes of solvent through the column. A subset of the column volumes exiting the column can be introduced to an accumulator, to immobilize thereon ligands having the preselected affinity, and eluting the ligand.

Compositions of the invention may optionally include adjuvants.

Advantages of the present invention include speed, reproducibility and automation. It is preferable to use particles capable of perfusion chromatography since perfusion particles allow the system to operate at very high flow rates while maintaining both high sample loading capacity and chromatographic resolution.

Figure 3:
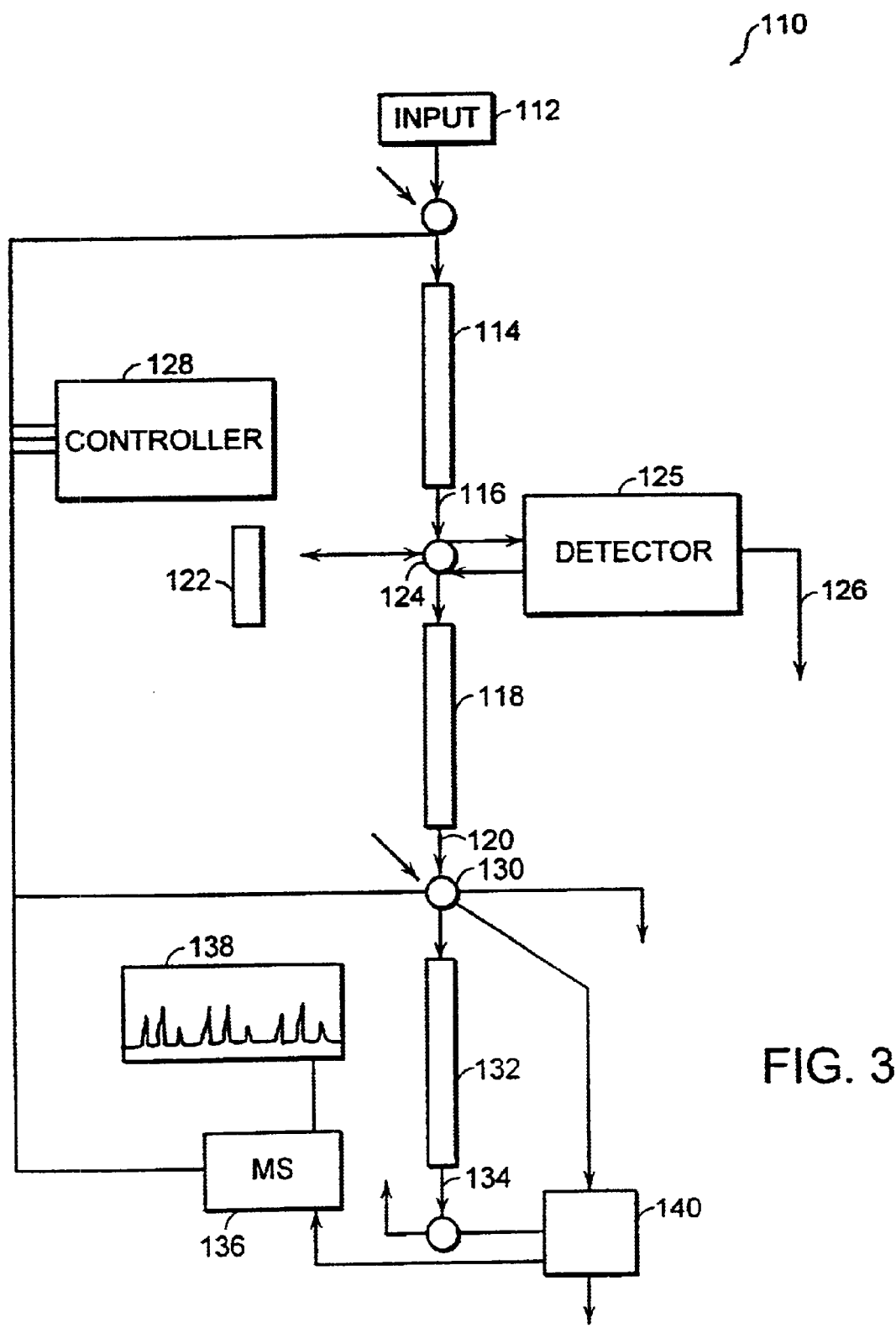
FIG. 3 is a schematic representations of a splitter interface (sampler) between a liquid chromatography column and a mass spectrometer in the apparatus of the invention (Position A).

As will be understood from the above description and the examples given below, the claimed invention is amenable to numerous configurations which may be chosen on the basis of the desired application or the sample. To further exemplify the invention, several configurations are enumerated in more detail below. In certain embodiments, as depicted in FIG. 3, the apparatus of the invention 10 comprises a sample input 112 for introducing sample into the apparatus 110 into a first column 114 to partition, based on a first physico-chemical property, candidate ligands, or complexes thereof with a target molecule, to generate a first exit stream 116. First exit stream 116 is optionally directed to a second column 118 to partition candidate ligands based on a second, different physics chemical property, to generate a second exit stream 120.

In various embodiments, there is optionally an interface 122 between the first column 114 and the second column 118 to condition the solvent in the first exit stream 116 for introduction into second column 118. Optionally, first multi-valved splitter 124 may be positioned between the first column 114 and second column 118 to direct the first exit stream 116 to the interface 122, to the detector 125, where, if ligand is present, exit stream 116 is reintroduced to valve 124, or if no ligand is present, exit stream 116 is directed to waste stream 126.

The multi-valved splitter 124 can be a rotary multi-port valve capable of two or more possible by-pass configurations and controlled by a sample controller 128.

Second exit stream 120 is optionally introduced into a second multi-valved splitter 130 which directs the second exit stream 120, into a third column 132. A sample of the third exit stream 134 containing a selected ligand may optionally be inserted into a third sample splitter 140, and then into a mass spectrometer 136 for determination of the charge to mass ratio of the ligand. A display 138 may be connected thereto.

In different embodiments, first column 114 is an affinity column for partitioning a library based upon a first physico-chemical property, and second column 118 is another affinity column to partition the first exit stream 116 based upon a second physico-chemical property. Third column 132 may be a reversed phase column capable of accumulating the desired ligand thereon prior to eluting the desired ligand into third exit stream 134.

In an alternative embodiment, first column 114 can be a dialysis or size exclusion system capable of partitioning based upon size. Second column 118 is an affinity column capable of partitioning based upon a second physicochemical property.

Figure 4:
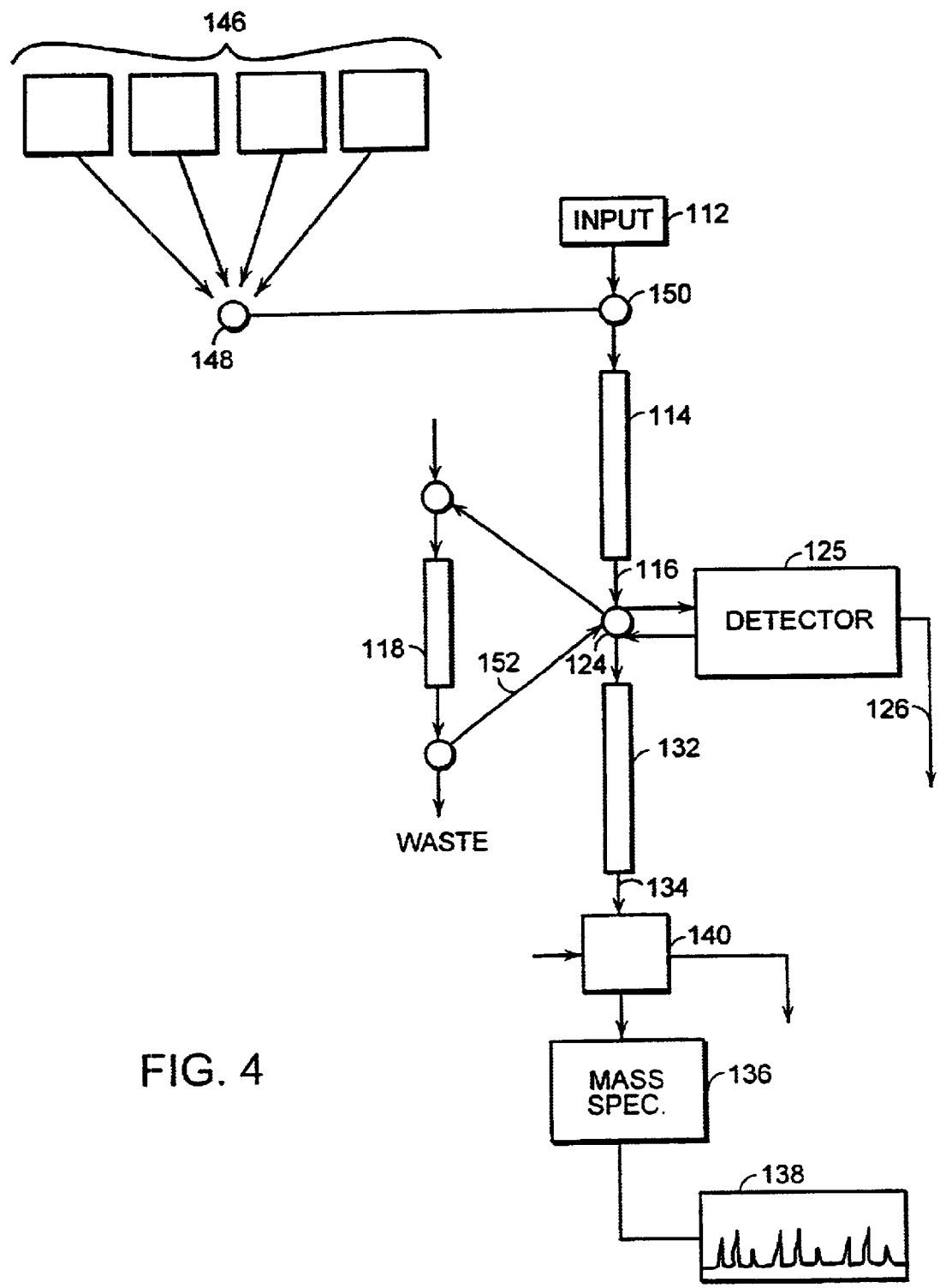
FIG. 4 is a schematic representations of a splitter interface (sampler) between a liquid chromatography column and a mass spectrometer in the apparatus of the invention (Position B).

In another exemplary configuration of the claimed apparatus, (FIG. 4) various solvent reservoirs 146 are connected via a valve 148 to a valve 150. Sample is introduced through the sample input 112, and combined with the solvent at valve 150. The solution is then introduced into first column 114, and the exit stream 116 can then be directed through a valve 124 to a detector 125, where, if ligand is present, exit stream 116 is reintroduced to valve 124, or if no ligand is present, exit stream 116 is directed to waste stream 126. Alternatively, or additionally, exit stream 116 may be introduced to a second column 118 suitable for diluting, desalting, or removing organic solvent from the exit stream 116 prior to reintroduction to the system through valve 124. Exit stream 152 is then introduced into third column 132. Third exit stream 134 can then be introduced to a splitter 140, and a sample directed to the mass spectrometer 136, and ultimately, the information is transmitted to an output display 138.

EXAMPLES

Example 1
Screening of a Synthetic Peptide Combinatorial Library (SPCL) Using an Antibody Against β-endorphin as a Target

Example 1A
Preparation of the Target Immobilized Affinity Column and the Control Column Monoclonal antibody (mAb) chosen (mouse IgG2a, clone 3E-7, Boebringer Manuheim, Indianapolis, Ind.) was raised against human β-endorphin and recognizes the amino terminus of β-endorphin, YGGFL (SEQ ID NO: 1). The purchased mAb (280 mg resuspended in 1 ml $H_2O$) was passed over an XL cartridge (2.1×30 mm) consisting of protein-G coupled to POROS™ perfusion chromatographic media (PerSeptive Biosystems, Framingham, Mass.) by making 10×100 ml injections on a BioCAD™ 20 Workstation (PerSeptive Biosystems, Framingham, Mass.). Protein-G binds to the Fc region of antibodies with high affinity. The mAb was subsequently cross-linked to the protein G using the standard methods and materials provided with the XL column. In brief, this consisted of passing 14 ml of cross-linking solution (100 mM triethanolamine, pH 8.5, 7.8 mg/ml dimethyl pimelimidate (DMP)) over the column at a flow rate of 0.5 ml/mm. The cross-linking reagent was quenched by subsequent injection of 2 ml of 100 mM monoethanolamine, pH 9.0. The sensor cartridge was washed with PBS, pH 7.4 at 0.5 ml/min for 2 min followed by a further injection of 2 ml of quench solution and washed as above. The antibody was efficiently immobilized to the column as demonstrated by the lack of reactivity to coomassie stain upon SDS-PAGE of the flow through. A second XL column (without antibody) was treated with cross-linking reagents and washed as for the affinity column for use as a "control column".

Figure 5:
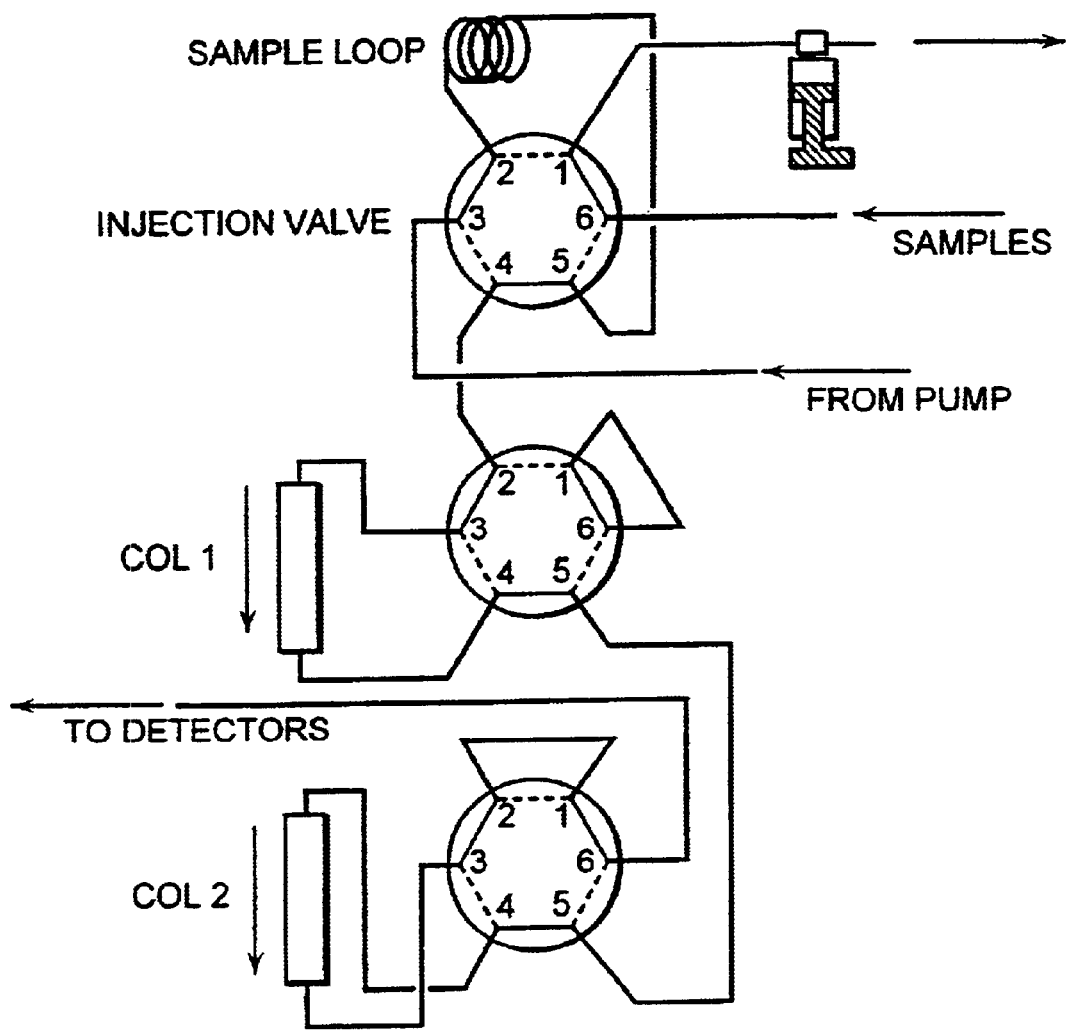
FIG. 5 is a diagram of a BIOCAD™ Workstation available from PerSeptive Biosystems, Inc. which is plumbed in tandem column mode. Column 1 is a weak anion exchange column and column 2 is a reversed phase column.

Example 1B
Control Screening of the Immobilized Target with the Known Epitope The target immobilized affinity column prepared above was plumbed in tandem mode to a vydac reversed phase C-18 column on a BioCAD™ Workstation using the configuration shown in FIG. 5. This configuration allowed independent equilibration and washing of the affinity and vydac columns while allowing in line elution of material bound to the mAb-column directly onto the vydac column. The reverse phase vydac column could then be eluted independently of the affinity column.

To investigate the binding of the immobilized antibody to its epitope YGGFL (SEQ ID NO: 1), the synthetic peptide YGGFL (SEQ ID NO: 1) (Sigma Chemical Co., St. Louis, Mo.; 1 mg/ml in PBS, pH 7.4) was injected onto the affinity column (flow rate 0.2 ml/mm). After washings with 10 column volumes (CV) of PBS, pH 7.4, the bound peptide was eluted from the affinity column with 12 mM HCl, directly onto the vydac C-18 column. This reversed phase column was then developed with a gradient of acetonitrile (4% ACN/12 mM HCl to 80% ACN/6 mM HCl over 18 min; flow rate 1 ml/min). Both columns were re-equilibrated in their respective starting buffers prior to the next injection.

Example 1C
Synthesis of the Soluble Peptide Combinational Library (SPCL)

The SPCL of general formula $NH_2$—XXXFL—COOH (wherein X represents any of the natural L-amino acids except cysteine and tryptophan) was synthesized as described (See Sebestyen, F. et, al. Bioorganic Med. Chem. Letts. 3; 413–418 ,1993) According to standard practice, the peptides were cleaved from the resin using "reagent B" and precipitated into ether. Calculations of the amount of each peptide gave a theoretical quantity of 70 nmols of each of the approximately 5832 potential sequence possibilities within the library (assuming equimolar coupling of each amino acid at each step in the synthesis and relatively equal recovery of each peptide for the ether precipitation). Sequences of either individual peptides obtained by immunoaffinity purification or "pool" sequence of the crude library were obtained by sequencing on a Hewlett Packard G1000A protein sequencer using standard HP2.2 chemistry (Hewlett Packard, Palo Alto, Calif.).

Example 1D
Control Binding Experiment

As a first step, whether the mAb immobilized onto the XL cartridge retained its ability to bind the peptide YGGFL (SEQ ID NO: 1) was investigated. The peptide solution (20 nmol) was injected onto the affinity column and then unbound peptide was removed by washing the column with PBS, pH, 7.4. Peptides affinity captured by the antibody was eluted from the "target column" directly onto the C-18 column for resolution. The amount of the peptide recovered, as calculated from the peak area, was approximately 1.2 nmoles. The theoretical capacity based on the quantity of mAb loaded onto the affinity column was 3.8 nmol demonstrating that approximately 25% of the binding sites of the mAb are available in a conformationally active form.

Example 1E
Determining the Capacity of the Target Immobilized Affinity Column The capacity of the column was examined by injecting increasing larger quantities of the peptide (YGGFL) (SEQ ID NO: 1) utilizing the loading template of the BioCAD™ Workstation. The amount of the bound peptide (as calculated from the peak height) reached saturation at about 1.2 nmoles. Interestingly, the amount of peptide bound to the antibody was independent of the flow used to inject the peptide. Increasing the flow rate from 0.2 ml/min to 5 ml/min did not affect the recovery. This result suggests a rapid interaction of the peptide with the antibody during the loading process when a perfusive packing material and elution conditions are used. The $EC_{50}$ value (50% of the saturating amount) for the peptide is approximately 30 nmols. This value correlates well with the affinity constants determined previously for binding of YGGFL (SEQ ID NO: 1) peptide to 3E-7 by competitive radiolabelled binding assays (See Lam et. al., *Biorganic Med. Chem. Letts.* 3:419–424 (1993).

Example 1F
Screening of the SPCL using the Target Immobilized Affinity Column

The diversity of the library was first assessed by running a small aliquot on the vydac C-18 column under the same conditions used for elution of bound material from the XL column. The large number of peaks exhibiting significant absorbance at the indicated wavelength are suggestive of the diversity of the library.

Using the conditions established for purified YGGFL (SEQ ID NO: 1) binding to the mAb column, the XXXFL library was screened for moieties recognized by the target immobilized mAb affinity column. The library (containing 2.8 nmols of each peptide) was loaded onto the "target column", the unbound material was washed with 10 Column volumes of PBS, pH 7.4. Finally, the affinity bound material was eluted directly onto the vydac C-18 column with 12 mM HCl. Elution of the C-18 column (with a 4–80% ACN gradient as described above) revealed approximately 10–12 resolvable peaks. The elution profile shows that, one of the peaks observed exhibits a retention time comparable to that observed for pure YGGFL (SEQ ID NO: 1). Using the chosen wash conditions (10 CV) for the immunoaffinity column, we were able to selectively discriminate a single moiety from a library with potentially greater than 5800 individual peptides. The identity of isolated YGGFL (SEQ ID NO: 1) was confirmed by mass spectrometry and peptide sequencing.

Example 1G
Control

In order to confirm the specificity of the target immobilized affinity column for YGGFL (SEQ ID NO: 1), samples of the purchased peptide and the library (XXXFL) were analyzed in a parallel experiment using the control column prepared in Experiment 1. The chromatogram was identical except for the peak corresponding to YGGFL (SEQ ID NO: 1). In a parallel experiment. a peptide with the sequence YEYFL (SEQ ID NO: 2) (a known non-binder to the mAb was not retained by the affinity column.

Example 2
Screening of a Peptide Combinatorial Library Employing Endotoxin (Lipopolysachharide) as a Target Example 2A
Preliminary Experiments Several agents, including some peptides, bind to endotoxin and reduce the lethal effects of this agent in animals. However, these agents are of limited use because of their inherent toxicity. A linear SPCL of the general structure FL (similar to the core region of Polymixin B (PmxB) was screened for moieties capable of binding to LPS and a cyclic library (of the general formula CXXXC) which is cyclized by virtue of the disulphide linkage between the two cysteine molecules.

We used a tandem column method employing POROS™ columns on a BioCAD™ 20 Workstation. Column 1 was a weak anion exchange column (PI/M; 4.6×100 mm) while column 2 was a reverse phase column (R2/H; 4.6×100 mm). A weak anion exchange column was chosen for column #1 since it has previously been demonstrated that agents capable of binding to LPS possess a degree of cationic character and hence would not necessarily be expected to bind to this column. It was initially demonstrated that the molecules pentamidine and polymyxin B (previously demonstrated to bind to the lipid A region of LPS) were retained on column 1 under the conditions used only after preincubation in the presence of LPS. LPS, however, would be expected to interact with this column due to the presence of two charged phosphate groups at the lipid A region of the molecule. Hence cationic molecules capable of binding to LPS would only be retained on column 1 if they were bound to this molecule. Material retained on column 1 was eluted directly onto column 2 where it was captured. Elution of column 2 allowed the resolution of peaks arising from column 1.

Example 2B
Synthesis of the XXXFL Library

The library XXXFL was made on Fmoc-Leu WANG resin using standard procedures in an Advanced Chemtech librarian peptide synthesizer. Prior to screening the library (consisting of approximately 5800 pentamers) it was divided into an anionic and cationic fraction based on retention on the weak anion exchange column (material binding to the column when injected in 50 mM tris, pH 6.7 was designated as the anionic fraction, while that passing through was the cationic fraction). Only the cationic fraction was screened using this paradigm. However, the cationic fraction represented >⅔ of the total library based on peak area for the two fractions.

Example 2C
Screening of the XXXFL Library

Screening the library for binding to LPS was performed as follows. The cationic fraction of the XXXFL library was incubated (30 min/RT) with 1–3 mg/ml of LPS (serotype O55;B5; Sigma Chemical Co., St. Louis, Mo.) in 50 mM Tris, pH 6.7. At this time the incubation mixture was injected and run over column 1 on the BioCAD™ Workstation (equilibrated in the same buffer). The column was run at 4 ml/min. After washing with the appropriate number of column volumes of equilibration buffer (1 CV=1.66 ml), the column was purged and eluted (using 8 mM HCl, 1M NaCl) directly onto column 2 by switching the latter column in line with column 1 during the elution process. Material captured on column 2 was eluted using a gradient from 12 mM HCl in water to 80% ACN, 6 mM HCl. Peaks were collected, further purified by rerunning on a vydac C-18 column (4.6×250 mm), and analyzed by Mass Spectrometry (on a Voyager™ MALDI-TOF instrument; PerSeptive Biosystems, Framingham, Mass.) and peptide sequencing (Hewlett Packard). Peptides identified were synthesized and binding of these molecules to the Lipid A region of the LPS was confirmed by measuring the ability of PmxB or Pentamidine to compete with the peptide for this site.

Furthermore, increasing the number of column volumes used to wash column 1 prior to elution onto column 2 resulted in a decrease in the subsequent recovery of these molecules, presumably due to dissociation of these agents from the LPS while on column 1. The number of wash volumes required to reduce the peak for these agents correlated with the reported affinities of these agents for LPS; PmxB (Kd 0.4 mM) was reduced 50% after 42 CVs washing of column 1 while pentamidine (Kd 100 nM) required a higher number of washes for a similar reduction (46 CVs).

Using this methodology we could rapidly examine which peaks from the library were capable of binding to LPS with the highest affinity since, upon exposure to higher numbers of wash volumes only the peptides with higher affinity for the target were retained. The relative reduction in the peak area (or height) for each peak eluted from the reverse phase column when plotted against the number of CVs used to wash column 1 could be used to distinguish the peaks with higher affinity since these showed a lower rate of reduction under the same conditions. Three such peaks from the XXXFL library and 3 peaks from the CXXXC library were further purified and characterized by MS and peptide sequencing. Results from the sequencing data for the XXXFL candidates suggested the structures RRRFL (SEQ ID NO: 3), RRKFL (SEQ ID NO: 4) or KKRFL (SEQ ID NO: 5). The latter peptide has been synthesized and demonstrated to bind to LPS using the same paradigm above. However, while this peptide is displaced by Pentamidine in a competition experiment, its affinity for LPS is much lower than the latter molecule. The other peptides will be synthesized and studied in a similar manner although another approach being considered is that a sublibrary of the format ZZZFL (where Z represents either R or K) be screened to identify the member with the highest affinity. Candidates purified from the cyclic library are still awaiting sequencing.

Example 2D

Affinity-Based Screening—Selection of High Affinity Binders—Effect of Wash Volumes Tandem columns consisting of an affinity column plumbed in-line to a reversed-phase (RP) column can be used to screen, libraries to select for binders of a known affinity based on the volume of washing of the affinity column.

A BioCAD™ Workstation was plumbed in the tandem column configuration. Column one was an immobilized rHsp70 affinity column (2.1×30 mm) and column two was a POROS™ R2 reversed-phase column (2.1×100 mm). The affinity column (column one) was washed with screening buffer before the library (natural protein digest library [PDL], 100 µg) was injected onto the affinity column at a flow rate of 0.2 ml/min. The affinity column was then washed with screening buffer in increasing numbers (5, 10, 20, & 40) of column volumes (CVs) at 02 ml/min. (1CV= 100 µL) The POROS™ R2 column was then switched in-line downstream of the affinity column. Bound material was eluted off the affinity column with acid directly onto the in-line RP column. The affinity column was then taken off-line and washed back into screening buffer. Finally, the POROS™ R2 column was eluted with an ascending acetonitrile gradient (0–80%) in TFA (0.1%).

Figure 6:
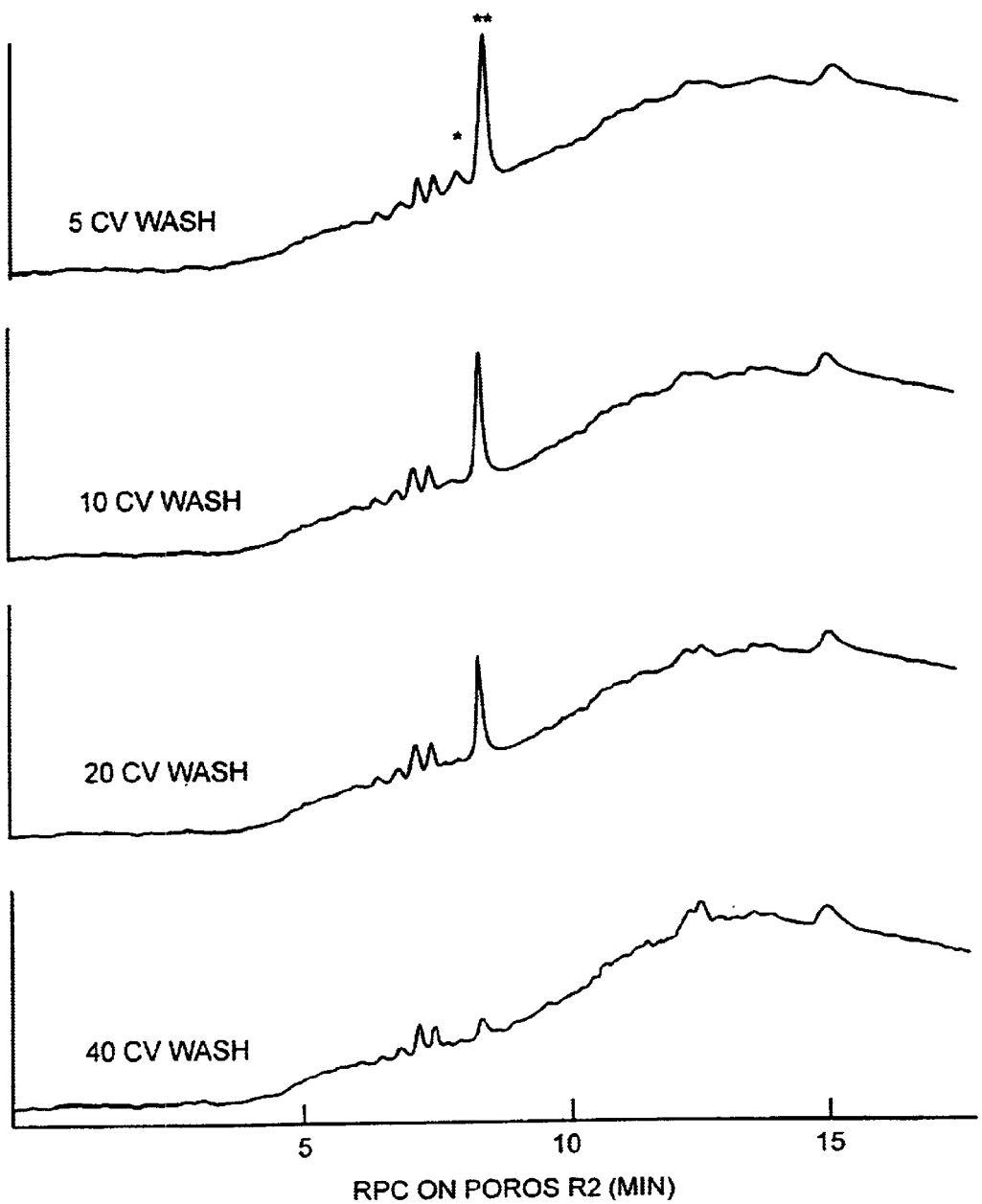
FIG. 6 depicts target-based screening of human rhsp70.
Figure 7A:
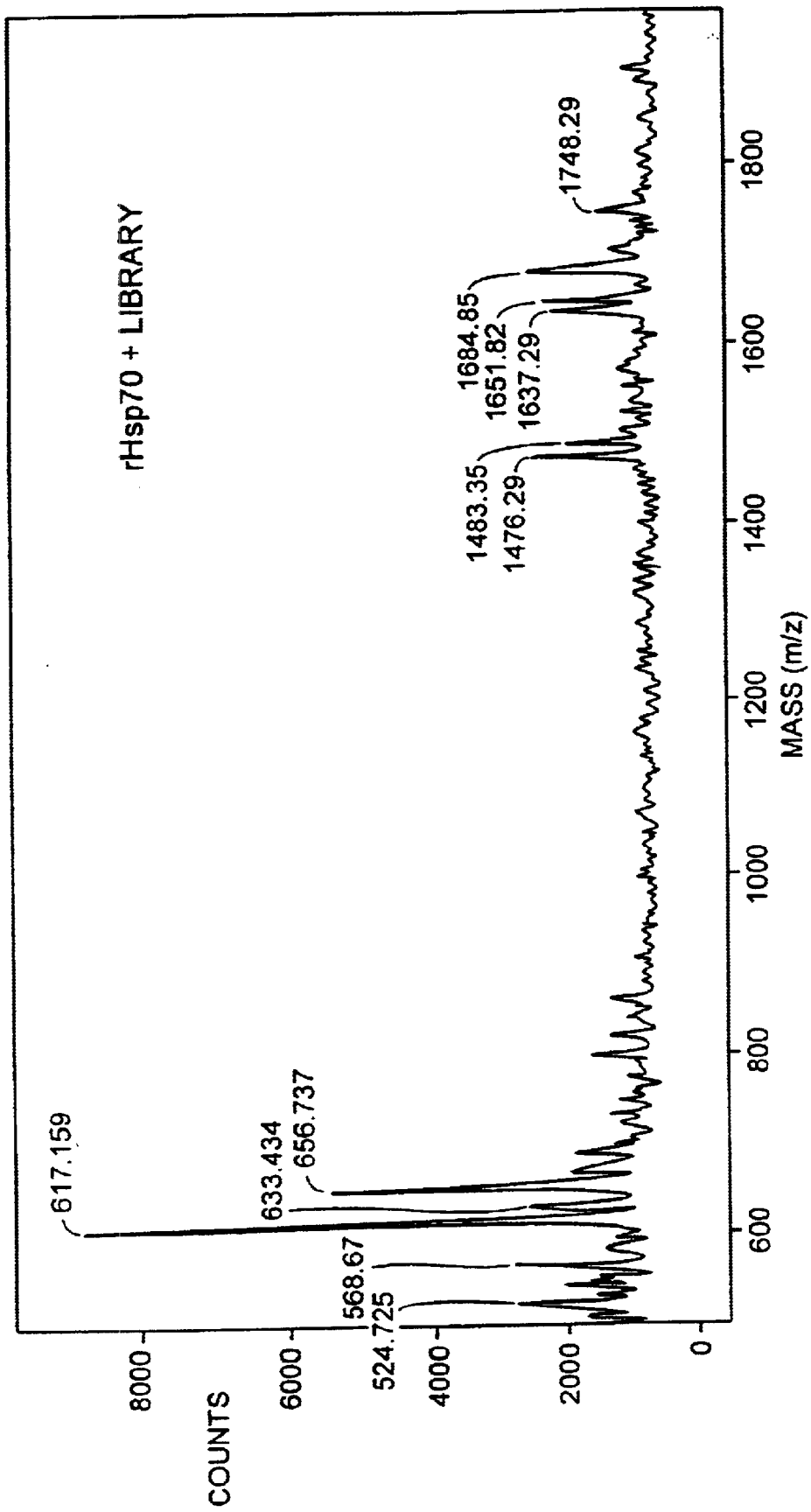
FIG. 7 depicts MALDI of natural peptide library screen vs. rhsp70 and Dnak.
Figure 7B:
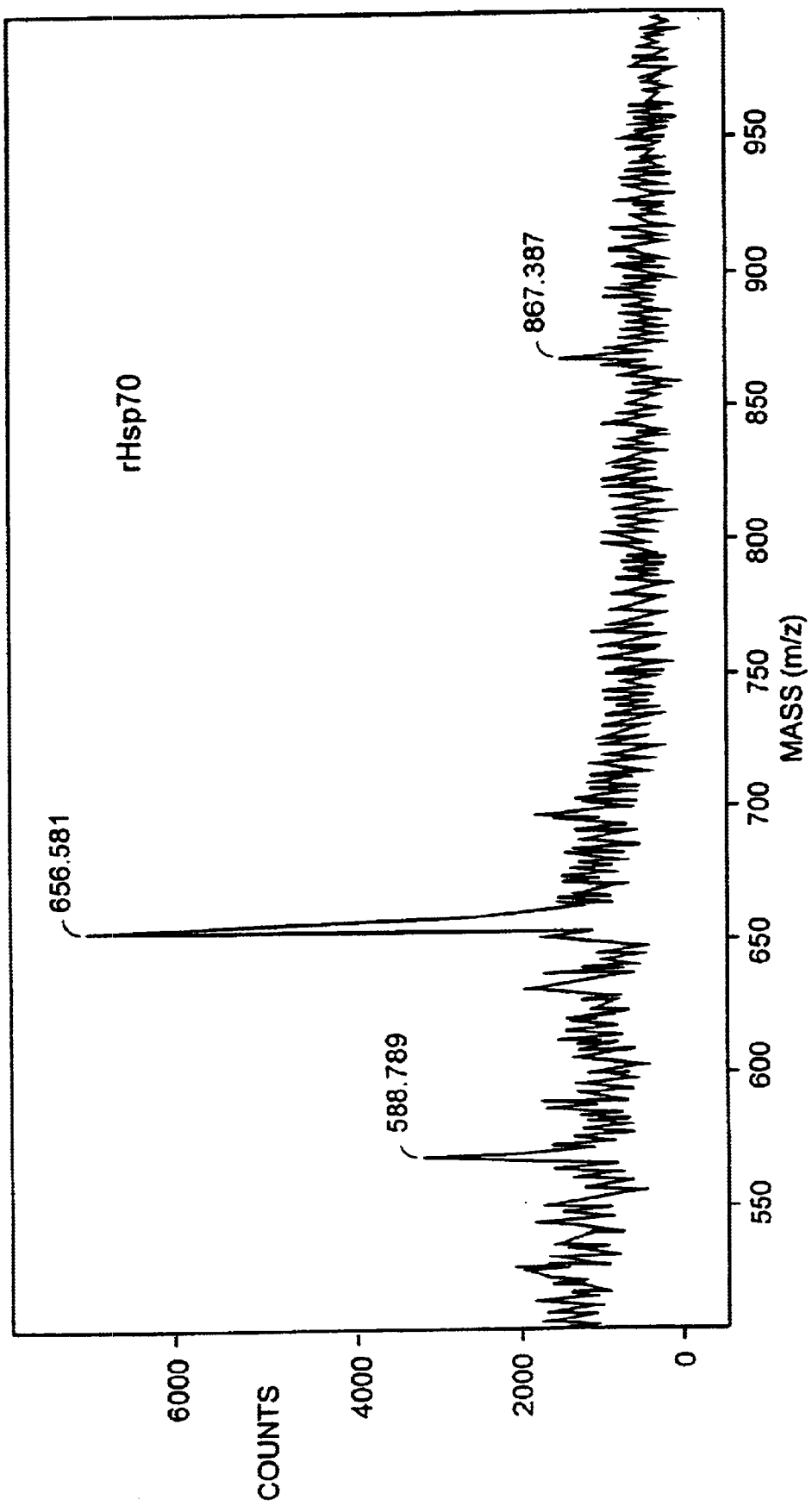
Figure 7C:
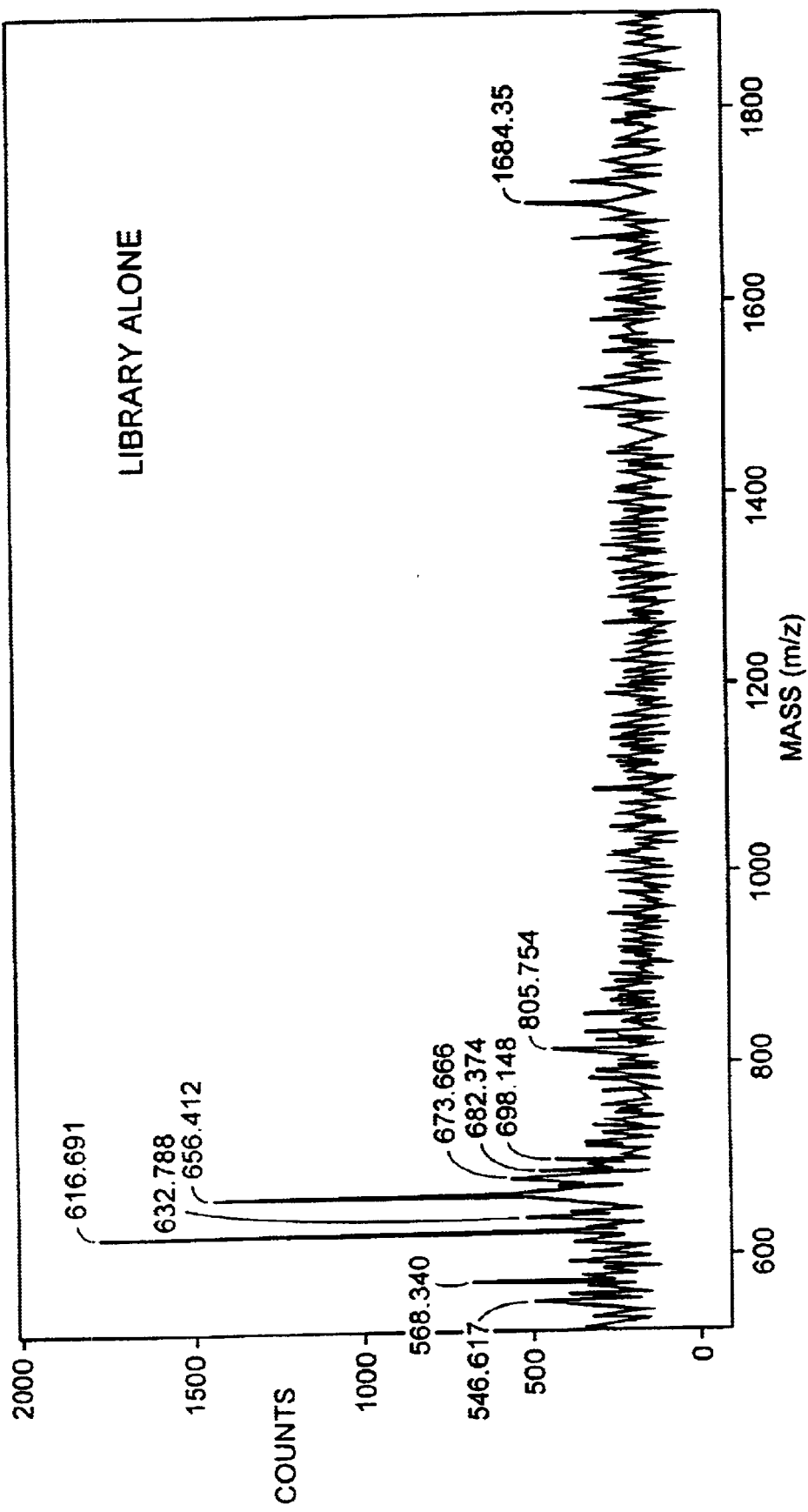
Figure 7D:
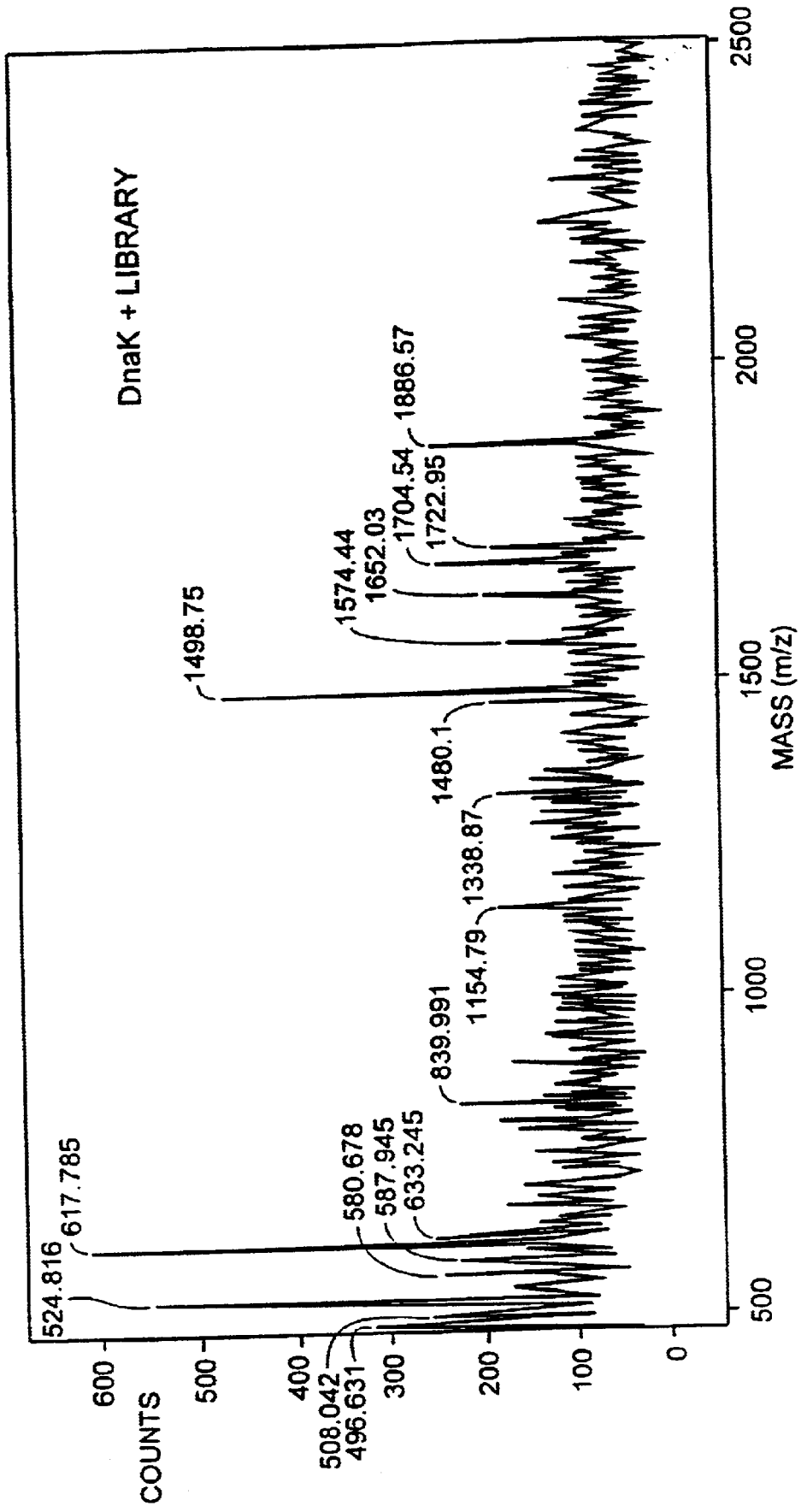

FIG. 6 shows the RP column portion of the experiment. At 40 CVs only a single peak is selected (**) suggesting that the protein represented by that peak has a high affinity for rHsp70. At lower wash volumes, e.g. 5 CVs, other peaks (*) are seen. These peaks are absent at 10 and higher CV washes, suggesting that they are low affinity binders.

Example 2E

Subtractive Screening-Selection of Target Specific Binders

A multi-target column format can be used to screen ligands for their ability to bind to a certain target and for their inability to bind to a second target in a single process. This technique should be generally applicable for selecting binders that differentiate between two different targets. For example binders can be selected that differentiate between wild type and mutant protein. For another example, ligands can be selected that bind to a pathogenic target but not to the homologous host target. Subtraction can be done in one chromatographic process or in parallel chromatographic runs with subtraction done at the analysis level.

A library has been screened using a SEC subtractive screening protocol with human Hsp70 as the host protein and its *E. coli* counterpart, DnaK as the pathogen target. A BioCAD™ Workstation was plumbed in the tandem column configuration. Column one was a size exclusion column (SEC) and column two a POROS™ R2 reversed-phase (RP) column (2.1×100 mm). Protein (50 µg) was pre-incubated with library (100 µg) and samples (100 µL) were injected onto the SEC at a flow rate of 1 ml/min. The protein peak was either collected for mass spec. analysis or the POROS™ R2 column was switched in-line downstream of the SEC. The protein peak was cut directly onto the in-line RP column, and the SEC was taken off-line. The POROS™ R2 column was then eluted with an ascending acetonitrile gradient (0–80%) in TFA (0.1%). Finally, the SEC was equilibrated back into screening buffer.

Total peptides eluted from rHsp70 and from DnaK were analyzed by MALDI-TOF. FIG. 7 shows the MALDI-TOF spectra for such experiments. A number of peaks are present in the rHsp70 sample incubated with the PDL (upper left panel of FIG. 7) that are not seen in the control incubations with rHsp70 (upper right panel) or PDL (lower right panel) alone. This indicates that these peptides are binding to rHsp70 itself or that there is insufficient separation of bound and unbound library. DnaK incubated with PDL (lower right panel) also binds peptides originating from this library. DnaK binds a different ensemble of peptides, although some are in common with rHsp70 (in bold).

Example 2F

Bimolecular Screening-Selection of Site-Specific Binders

Tandem columns consisting of an affinity column plumbed in-line to a RP column can be used to screen libraries for ligands that bind to a specific site on the target molecule via comparison of the eluents from a column containing both target molecule and a known ligand with the eluents from a column containing only target molecule.

The lectin Concanavalin A (Con A) has been used. Ligands were screened for specific binding to the sugar site of Con A as an example of the bimolecular approach to screening a mixture of components for interaction with a target. Biotinylated succinyl Con A was immobilized onto a streptavidin POROS™ support (BA cartridge, 2.1×30 mm). A library, consisting of the sequence XXXXX (where X represents any of 20 natural amino acids excluding cysteine) was passed over the affinity column, and material interacting with this support was subsequently eluted and captured on a RP column. In order to identify ligands that had specificity for the sugar-binding site, the peptide library was passed over the test column in the presence and absence of a ligand for Con A (methyl-α-D-mannopyranoside, 33 mg/ml). After exposing the column to 10 CVs of CAB buffer (0.2 m/min.), the remaining peptides were acid eluted onto a RP column. These peptides were eluted from a RP HPLC column using an acetonitrile gradient and the fractions were collected, pooled and sequenced. Recovery of each amino acid was expressed as a percentage of the total amount of amino acids recovered at each cycle of sequencing (AA %). Amino acid enrichment was then expressed for each amino acid as follows:

$$AA \text{ enrichment (Cycle } X) = \frac{AA \% \text{ (cycle } X) \text{ from test column (in absence of sugar)}}{AA \% \text{ (cycle } X) \text{ from test column (in presence of sugar)}}$$

The recovery of each AA from each cycle could thus be ranked and the sequence of the 5-mer peptide with the sequences exhibiting the greatest recoveries of AA at each cycle was 'named' from this data.

FIG. 8 shows the results of this data. From this data we 'named' the peptide HHRSY (SEQ ID NO: 6) as being composed of the amino acids that showed the greatest increase in AA % when the column lacked sugar relative to its AA % in the presence of sugar. Synthesis of this peptide and characterization of its ability to bind revealed that it was capable of binding specifically to Con A immobilized on the column with little binding to the control column. Furthermore, this peptide could be displaced somewhat by inclusion of a high concentration of the competing sugar ligand. These data suggest that it is possible to identify ligands for a specific site on a molecule by using this bimolecular approach to screening.

Example 2G

IgG Purification

Immobilized protein A and protein G are traditionally used for purification of immunoglobulins (IgG) from serum, ascites, hybridomas and cell culture supernatents. This example provides an alternative approach to proteins A & G, since immobilized proteins tend to leach from the column and are incompatible with the acidic conditions required for elution of bound IgG.

To screen for IgG as target, peptide libraries were generated from each of the following sources: 1) Natural Peptide Libraries of generic proteins, 2) Polyclonal Antibody Libraries, and 3) Protein A and G digests. Each of the above libraries were screened for peptides that bound specifically to mouse IgG (whole molecule) or mouse IgG, Fc fragment. One of two screening procedures were followed: i) Solution phase peptide(s) screening or ii) solid phase peptide screening. Solution phase peptide screening involved incubating the peptide library with mouse IgG (whole or the Fc fragment) in solution and separating the IgG and bound peptides from the unbound peptides by and further separation of the protein and bound peptides by conventional reversed phase chromatographic techniques under acid conditions. Solid phase peptide(s) screening involved passing the peptide library through an immobilized IgG column under physiological conditions and eluting the bound peptides into a RP HPLC column under acidic conditions. The peptide(s) selected by either one of the above screening methods were characterized by mass spectrometry (MALDI-TOF) and Edman sequencing methods. The peptide(s) were then immobilized on POROS™ media and evaluated for specificity, selectivity and capacity to bind IgG from serum. Various coupling chemistries (direct synthesis or off-line immobilization), the effect of ligand density, the activation chemistry, and the nature of interaction with IgG were investigated for some of the selected peptide(s).

Example 3

Screening

All proteins and reagents for buffers were obtained from Sigma Chemical Co (St. Louis, Mo.) unless otherwise specified. Anti-IgG (Fc specific) antibodies were purchased from Biodesign International (Kennebunk, Me.). Screening by SEC and RP Chromatography was performed on the INTEGRAL™ chromatography Workstation (PerSeptive Biosystems, Inc., Framingham, Mass.). Screening by immobilized target (IgG) column in tandem with RP column was performed on the BiOCAD™ 20 Workstation (PerSeptive Biosystems, Inc., Framingham, Mass.). Size exclusion column (Superdex 200 HR 10/30, molecular exclusion limit 150,000 daltons to 6000 daltons) was obtained from Supelco (Bellefont, Pa.). Vydac RP $C_{18}$ column (4.6 mDxmmL) was obtained from Separation Science, Hesperia, Calif. POROS™ Self Packing device, POROS™-Protein A, POROS™ HQ and POROS™ CM columns were obtained from PerSeptive Biosystems (Framingham, Mass.). Mass spectral analysis was performed on the Voyager™ BioSpectrometry Workstation with linear analyzer and a 337 nm Nitrogen laser, from PerSeptive Biosystems, Inc./Vestec Mass Spectrometry Products, Framingham, Mass. Peptide sequencing by Edman degradation was done on the Hewlett Packard Series II 1090 liquid Chromatograph. SDS gel electrophoresis kit was obtained from Novex Biochemicals (San Diego, Calif.).

3A: Generation of Peptide Library

1) Natural Peptide Library

The protein list used for generating the peptide library is enclosed. 60 mgs of each of the 23 proteins were mixed with 6N guanidium chloride at room temperature for half hour. 36 mM EDTA and 30 mM dithiothrietol were added to the mixture and incubated at room temperature for an additional one hour. After denaturation of proteins and reduction of disulfides, 30 mM iodoacetamide was added to the mixture which was then incubated at 37° C. overnight with constant shaking. The protein mixture was dialyzed, lyophilized and divided into three batches for enzymatic digestion at 37° C. for 24 hrs. One batch was treated with trypsin (protein to trypsin ratio 25:1 w/w), the second batch was treated with chymotrypsin (protein to chymotrypsin ratio 15:1 w/w) and the third batch was treated with both trypsin (1:25 w/w) and chymotrypsin (1:15 w/w). The digestion buffer used was 0.1 M ammonium bicarbonate buffer containing 0.12 mM calcium chloride (pH 8.3). After 24 hrs, the three batches were heat treated at 90° C. for 30 min. to inactivate the enzymes. The efficiency of digestion was assessed by RP chromatography and SDS-polyacrylamide gel electrophoresis.

2) Anti-IgG (Fc specific) polyclonal antibodies Library

Anti-IgG (Fc specific) polyclonal antibodies were obtained from rabbit, goat and sheep. 30 mg of each of the polyclonal antibodies were denatured, reduced and alkylated as described above. The mixture was treated with trypsin (1:25 enzyme:protein ratio) and the digests were pooled and lyophilized.

3) Protein A and G Digests 1 mg each of recombinant Protein A and G were denatured, reduced and alkylated as described above. The denatured proteins and 15 mgs each of native proteins A and G were treated with trypsin (1:25 enzyme:protein ratio) and chymotrypsin (1:15 enzyme:protein ratio) overnight as described above. The resulting mixture of native and denatured digests were pooled and lyophilized.

3B: Diversity of the Peptide Library

To determine the diversity of each the peptide libraries, the sequences of all the proteins used to generate a library were obtained via the Entrez program and retrieved into the GPMAW program. The GPMAW program simulates the enzymatic digestions and generates information on the number, sequences and masses of all the possible peptides generated by such three batch digestion. This information was very valuable in predicting the extent of diversity and confirming the source, mass and sequence of the peptide(s) obtained after the screening.

3C: Immobilization of IgG(s)

1 mg POROS™ EP (epoxy) was suspended in 5 ml 0.1 M phosphate buffer (pH 9) containing 20 mg IgG. After the beads were well suspended, 4 ml 0.1 M phosphate buffer (pH 9) containing 2 M $NA_2SO_4$ were added to the mixture and it was shaken overnight at room temperature. The beads were then washed with 10 mM PBS (pH 7.5) and stored in the refrigerator before they were packed into columns.

3D: Peptide Screening Protocol

1) Solution Phase Peptide(s) Screening through Size Exclusion—Reversed Phase Columns 5 mg each of either mouse IgG (whole) or the Fc fragment was incubated with 20 mg of natural library and protein A and G digests, respectively. The mixture was dissolved in 1 ml of a mixture of 25 mM sodium phosphate buffer and 0.15 M NaCl (pH 7) overnight at 4° C. After incubation, several chromatographic runs through the Superdex SEC and RP columns were conducted with 200 of the protein and peptide mixture injected through the Superdex column during each run. The flow rate for the Superdex column was 0.75 m/min with the 25 mM sodium phosphate buffer and 0.15 M NaCl (pH 7) mixture. The early eluting protein peak was collected directly onto the RP column. The remaining portion of the peak was washed off the SEC. The mouse IgG (whole) or Fc fragment and its associated peptides were then eluted from the RP column under the following conditions:

| | |
|---|---|
| Flow rate: | 1 ml/min, |
| solvent A: | 0.1% TFA/DIW |
| solvent B: | 0.1% TFA/85% ACN/15% DIW |
| Gradient conditions: | 0–100% B for 30 CVs. |
| | 01.5 ml fractions were collected and lyophilized. |

The following controls were run through the SEC-RP columns under similar conditions:

| | |
|---|---|
| Control 1: | Pooled peptide digests through SEC with cut off at the elution volume of mouse IgG (whole) or Fc fragment. This serves as a control for coeluting peptides. |
| Control 2: | Mouse IgG, (whole) or the Fc fragment through columns. This serves as a control for any peptides/fragments arising due to protein degradation. |
| Control 3: | Blank run of 0.1% TFA/DIW run through Rp column to ensure that the column was clean. |

Fractions corresponding to bound peptide peaks were lyophilized and redissolved in 1001 of 0.1% TFA/DIW for mass spec analysis by MALDI-TOF.

2) Solid Phase Peptide(s) Screening with Immobilized Target and Reversed Phase Columns in Tandem The IgG activated POROS™ was packed into 4.6 mm D×100 mm L PEEK columns using Self Pack® assembly on BioCAD™ at 20 ml/min flow rate. 5 to 50 mgs peptide library (natural peptide library or polyclonal antibody digest) dissolved in 0.5 to 2.5 ml of 10 mM PBS (pH 7.5) was injected onto the column at flow rate of 0.5 ml/min. After wash with 5 CVs of PBS, the bound portion was eluted with 10 mM HCl and collected manually. The fraction was concentrated down to approximately 500 µl and at least 80% of it was injected onto a 4.6 mm D×250 mm L Vydac C18 column at 1 m/min. The RP column was equilibrated with 0.1% TFA/DIW and peptides were eluted with 15 CVs of a 0–40% acetonitrile gradient at flow rate of 1 ml/min. 1 ml fractions were collected. The fractions corresponding to the bound peptides were concentrated in Speed Vac and analyzed by MALDI-TOF and Edman sequencing. As a control for non-specific binding, the peptide library was run through a POROS™ OH column (no IgG) in line with the RP column.

3E: Analyses

1) Matrix Assisted Laser Desorption-Time of Flight Mass Spectrometry (MALDI-TOF MS)

Matrix used was α-cyano-4-hydroxycinnamic acid dissolved in 1 ml of 50% acetonitrile in 0.1% TFA/deionized water. Bradeykinin and insulin were used as external standards for calibration.

2) Edman Sequencing: was done on HP 1090 sequencer with standard protocol.

3F: Surface Design and Affinity Chromatography

1) Immobilization of Peptides via N-terminal End 1 g POROS™ AL (aldehyde) was suspended in 10 mM PBS (pH 7.5) containing 100 mg sodium cyanoborohydride ($NaCNBH_3$). 5 to 20 mg of each of the peptides selected by various screening procedures was added to the resin and the mixture was shaken overnight at room temperature. 100 mg sodium borohydride ($NaBH_4$) was then added and the mixture was shaken for another 2 hrs. The beads were then washed with PBS and packed into 4.6 mm D×100 mm L column using POROS™ Self Pack® device.

2) Direct Synthesis of Neptides on POROS™

The 19-mer peptide (TVTEKPEVIDASELTPAVT) (SEQ ID NO: 7) selected from protein A and G digests was directly synthesized on 20 µm amine-functionalized™ particles by standard FMOC chemistry. About 700 mg of resin was dry packed into a 4.6 mm D×50 mm L PEEK column equipped with 2 µm frits. The packed column was attached with appropriate adapters to a PerSeptive Biosystems 9050 plus continuous flow peptide synthesizer. Upon completion of synthesis, the resin was dried and deprotected using 95% TFA/5% triisopropylsilane for 24 hrs. The final peptide-support conjugate was packed using POROS™ Self Pack® column packing device at flow rate 10 ml/min onto 4.6 mm D×50 mm L column for evaluation as affinity supports.

3G: Analytical Methods

1) Purification of IgG (Whole) from Human Serum on Peptide Column

100 µl of 1:10 diluted serum was injected onto the peptide column which was equilibrated with 20 mM tris (pH 8.0) at 5 ml/min. The bound proteins were eluted with 0–1 M NaCl gradient in 15 CVs. Fractions were collected manually and concentrated by Speed Vac for subsequent analysis by SDS-polyacrylamide gel electrophoresis.

2) Purification of IgG (whole) from human serum on POROS™-Protein A column

100 µl of 1:10 diluted serum was injected in the protein A column, which was equilibrated with 10 mM phosphate buffer containing 0.15M NaCl (pH 7.5) at a 5 ml/min flow rate. After injection and 5 CVs wash, the bound portion was eluted in a single step with 10 mM HCl. The bound fractions were collected and analyzed by SDS-Polyacrylamide gel electrophoresis.

3) Purification of IgG (whole and Fc fragment) on POROS™-peptide (TVTEKPEVIDASELTPAVT) (SEQ ID NO: 7) column The 19-mer peptide column (4.6 mm D×50 mm L) was equilibrated with 20 CVs of equilibration buffer, 20 mM tris (pH 7). About 500 μl of 1 mg/ml of each of the following samples was injected onto the 19-mer peptide column (4.6 mm D×50 mm L): 1) pure IgGs from either human or mouse or chicken, 2) IgA (whole molecule), 3) human serum, 4) fetal bovine serum (1:10 dilution), or 5) 500 μl of 1 mg/ml mouse Ige, Fe fragment. After injection, the column was washed with 20 CVs of a mixture of 20 mM tris buffer and 0.4 M NaCl (pH 7). The remaining bound proteins were eluted with 20 CVs of 12 mM HCl. Experiments with control POROS™—$NH_2$ (no peptide) column were done similarly. The bound fractions were collected and analyzed by SDS-Polyacrylamide gel electrophoresis.

4) Purification of Human IgG (whole) and Mouse IgG (Whole and Fc Fragment) on POROS™-Protein A Column POROS™-Protein A column (2.1 mm D×30 mm L) was equilibrated with 20 mM tris (pH 7) for 20 CVs. About 500 μl of 1 mg/ml of each of the following samples was injected onto the POROS™-Protein A column (2.1 mm D×30 mm L): 1) pure human IgG (whole molecule), 2) human serum (1:10 dilution), and 3) 500 μl of 1 mg/ml mouse IgG, Fc fragment. After injection, the column was washed with 20 CVs of a mixture of 20 mM tris buffer and 0.4 M NaCl, (pH 7). The remaining bound proteins were eluted with 20 CVs of 12 mM HCl. Experiments with control POROS™-OH column (no peptide) were done similarly. The bound fractions were collected and analyzed by SDS-Polyacrylamide gel electrophoresis.

5) SDS Polyacrylamide Gel Electrophoresis

SDS-polyacrylamide gel electrophoresis of the salt and acid eluted bound fractions were run on 4–20 % or 12% (1 mm×10 cm) tris glycine precast gels under reducing conditions. Sample preparation, staining and destaining were done according to the manufacturer's recommendation.

Natural Peptide Library

Both solution phase and solid phase peptide(s) screening of mouse IgG (whole fragment) with the natural peptide library yielded one peptide of mass 1633 daltons and amino acid sequence CAQCHTVEK (SEQ ID NO: 8). Database search revealed that this peptide is a tryptic digest of cytoebrome c (one of the proteins in the library) with a heme group covalently attached to the two cysteines at amino acid positions 14 and 17 of the protein.

The CAQCHTVEK (SEQ ID NO: 8) peptide with heme group was immobilized on POROS™AL® (aldehyde) via the N-terminal end. This POROS™-peptide conjugate was used to separate IgG from serum at pH 8 under a 0–1 M NaCl gradient. At pH 8, IgG was purified with comparable purity to that of IgG separated on POROS™-Protein A column. The capacity of the POROS™-peptide column was determined to be 10 mg/ml column volume which is comparable to the binding capacity of POROS™-Protein A column. To determine the nature of interaction, the purification profile of IgG separated on the POROS™-peptide column was compared with the IgG purified on standard ion exchange columns such as POROS™-CM and POROS™ HQ. Results indicated that, under similar conditions, peptide columns exhibit predominantly ion exchange characteristics with secondary hydrophobic interactions and have a higher selectivity for IgG from serum than either of the ion exchange columns. The effect of the varying loading densities of peptide (from 10 mg/g POROS™ to 100 mg/g POROS™) on specificity and capacity for IgG binding was also investigated. The specificity of the peptide for IgG binding was also investigated. The specificity of the peptide for IgG did not vary with varying ligand densities, but the nature of interaction of IgG varied. At low loading density (10 mg/g POROS™) IgG bound primarily via ionic interaction requiring elution of bound IgG with salt gradient. At higher loading density (100 mg/mg) IgG bound strongly and eluted with acid buffer. The binding capacity varied from 1–2 mg/ml column volume at lower ligand density to 30 mg/ml column volume at higher ligand densities. The heme peptide POROS™ bound very weakly to HSA and only under very hydrophobic conditions (200 mM sodium sulphate, pH 7 buffer).

When the heme peptide was immobilized via the carboxyl groups of heme and the free C-terminal end, no IgG binding was seen indicating that free carboxyl groups of the peptide were very important for binding to IgG.

A simplified analog of the heme peptide (GAQGHTVEK) (SEQ ID NO: 9) was synthesized and immobilized on POROS™ AL via the N-terminal end. At pH 8, this GAQGHTVEK (SEQ ID NO: 9)-POROS™ conjugate bound specifically, and with comparable purity, to the IgG purified from human serum on POROS™-Protein A column. The bound IgG was eluted from the GAQGHTVBK (SEQ ID NO: 9)-POROS™ column with 100 mM NaCl. The IgG binding capacity was determined to be 5 mg/ml column volume. Loading densities from 20 mg/g to 40 mg peptide /g POROS™ were evaluated. At these ligand densities, the specificity of IgG binding was not affected, but the capacity was reduced.

Protein A and G Digests

The Fc binding domain of recombinant proteins A and G and the amino acids involved in the binding of protein A to IgG have been mapped by site-directed mutagenesis (Fahnestock, S. R., Alexander, P. Nagle, J. and Filpula, D., J. Bacter (1986) 167(3):870–880). However, there has been no report of peptides isolated from these bacterial proteins that bind to IgG. By solution phase peptide(s) screening with native and denatured recombinant protein A and G digests against mouse IgG (Fc fragment) four peptides with remarkable overlapping sequences were identified. The peptide(s) were as follows: TVTEKPE (SEQ ID NO: 10), EKEPEVID (SEQ ID NO: 11), GDAPTPEKEPEASI (SEQ ID NO: 12) and TVTEKPEVIDASELTPAVT (SEQ ID NO: 7). The sequences of the larger peptides correlated with mass spec data. None of these peptides are typical tryptic digests, indicating that these peptides probably were selected from the native protein G digest. Database search revealed that all of these peptides were from recombinant Protein G. Further, the TVTE (SEQ ID NO: 13) sequence is a part of the Fc binding domain of recombinant protein G.

The TVTEKPEV (SEQ ID NO: 14) peptide was synthesized and immobilized on POROS™ via the N-terminal end. This POROS™-TVTEKPEV (SEQ ID NO: 14) was found to bind IgG from human serum at pH 8 with comparable specificity as the POROS™-Protein A conjugate. The bound protein was eluted with 0–1 M NaCl gradient. The TVTEK-PEVIDASELTPAVT (SEQ ID NO: 7) peptide was synthesized directly on POROS™. $NH_2$ resin via the C-terminal end. This peptide bound mouse IgG, Fc fragment with low capacity but high selectivity. The bound IgG was eluted with acid buffer. This peptide was more selective for IgG than IgA. Human IgG bound more selectively to the 19-mer peptide column that IgG from rabbit, goat or mouse.

One of the important and novel features is that from proteins A & G known to bind IgG with high affinity and requiring acidic conditions to elute the bound IgG, peptides were isolated, at least one of which (TVTEK) (SEQ ID NO: 15) has been shown to bind IgG, but with less affinity requiring only salt gradient for elution of the bound protein. Second, the peptide(s) of varying affinities and selectivity towards IgGs from different species have been identified.

Third, it is remarkable that two of the peptides namely, TVTEKPEVIDASELTPAVT (SEQ ID NO: 7) and TVTEKPEV (SEQ ID NO: 14) are part of the Fc binding domain of recombinant protein G.

Polyclonal Antibody Digests

Polyclonal antibodies are an interesting and logical source of peptides since they have specific antigen binding sites. A synthetic antibody fragment against lysozyme has been used as a ligand in immunoaffinity chromatography. This fragment was generated by molecular modeling of lysozyme and its antibody (Welling, G. W. et al., (1990) *J. Chrom.*, 512:337–343). Single chain antibodies that bind with weak affinities have also been generated against many targets by phage display (Griffiths, A. D. et al., (1994) *The EMBO J.* 13(14):3245–3260). To date there has been no report of selection of target specific peptide(s) isolated from polyclonal antibody digests. Tryoptic digests of denatured anti-IgG (Fc specific) polyclonal antibodies raised in rabbit, goat and sheep were run through a POROS™ epoxy column immobilized with IgG. The bound peptides were eluted onto an RP column and characterized. The amino acid sequence was determined to be GAQGIITVEK (SEQ ID NO: 9). A database search revealed that the GAQGHTVEK (SEQ ID NO: 9) sequence is a part of the variable region of the light chain of IgG. Note that the HTVEK (SEQ ID NO: 16) motif is also found in the heme peptide of cytochrome c. The heme peptide has been shown, as above, to bind IgG. Additionally, the TVEK (SEQ ID NO: 17) motif is similar to the TVTEK (SEQ ID NO: 15) sequence found in the IgM heavy chain, T-cell receptor (beta chain) and also IgG binding proteins such as protein G and protein LG. Protein LG, a hybrid molecule of protein L and G, binds to intact IgGs, as well as Fc and Fab fragments and IgG light chains. The characteristics of GAQGHTVEK (SEQ ID NO: 9) peptide as affinity surface for IgG binding have been discussed above. The most important and novel feature is that from a mixture of denatured antibodies, one peptide was isolated that was selective for IgG.

By choosing different libraries, peptides have been chosen that selectively bind to different portions of IgG (either the Fab or the Fc fragment). There is remarkable similarity in the sequences of some of the IgG binding peptide(s) isolated from different protein sources. None of these peptides were shown to bind IgG previously. The specificity of the peptide (s) for IgGs from various species varies depending on the orientation, activation chemistry and the density of immobilized ligand. Finally, this invention provides proof of the concept that both chromatographic peptide(s) screening technologies (solid phase and solution phase) are comparable and yield credible results.

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: synthetic
      peptide corresponding to the amino terminus of
      Beta-endorphin

<400> SEQUENCE: 1

Tyr Gly Gly Phe Leu
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Tyr Glu Tyr Phe Leu
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Arg Arg Arg Phe Leu
 1               5
```

```
<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Arg Arg Lys Phe Leu
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Lys Lys Arg Phe Leu
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

His His Arg Ser Tyr
 1               5

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence:Protein
      fragment derived from a tryptic digest of protein
      A and G

<400> SEQUENCE: 7

Thr Val Thr Glu Lys Pro Glu Val Ile Asp Ala Ser Glu Leu Thr Pro
 1               5                  10                  15

Ala Val Thr

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Protein
      fragment derived from a tryptic digest of
      cytochrome c.

<400> SEQUENCE: 8

Cys Ala Gln Cys His Thr Val Glu Lys
 1               5

<210> SEQ ID NO 9
<211> LENGTH: 9
<212> TYPE: PRT
<213> ORGANISM: Artificial Sequence
```

```
<220> FEATURE:
<223> OTHER INFORMATION: Description of Artificial Sequence: synthetic
      peptide

<400> SEQUENCE: 9

Gly Ala Gln Gly His Thr Val Glu Lys
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:Protein
      fragment derived from the tryptic digest of
      protein A and G

<400> SEQUENCE: 10

Thr Val Thr Glu Lys Pro Glu
  1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Protein
      fragment derived from the tryptic digest of
      protein A and G

<400> SEQUENCE: 11

Glu Lys Glu Pro Glu Val Ile Asp
  1               5

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Protein
      fragment derived from the tryptic digest of
      protein A and G

<400> SEQUENCE: 12

Gly Asp Ala Pro Thr Pro Glu Lys Glu Pro Glu Ala Ser Ile
  1               5                  10

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Part of the
      Fc binding domain of a recombinant protein G

<400> SEQUENCE: 13

Thr Val Thr Glu
  1

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide  corresponding to a part of the Fc binding
      domain of recombinant protein G

<400> SEQUENCE: 14
```

```
Thr Val Thr Glu Lys Pro Glu Val
  1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Protein
      fragment derived from the tryptic digest of
      protein A and G

<400> SEQUENCE: 15

Thr Val Thr Glu Lys
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:Motif found
      in part of the variable region of the light chain of
      IgG.

<400> SEQUENCE: 16

His Thr Val Glu Lys
  1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:Motif with
      similarity to TVTEK

<400> SEQUENCE: 17

Thr Val Glu Lys
  1
```

What is claimed is:

1. A method of analyzing the relative binding affinities of at least a first ligand and a second ligand to a target using a tandem column chromatography system, the method comprising the steps of:
   (a) providing a solution comprising a plurality of mixed ligands and a target, wherein the plurality of mixed ligands comprises at least a first ligand and a second ligand;
   (b) introducing a sample of the solution to a first column, the first column comprising a size exclusion medium;
   (c) passing a number of column volumes of a solvent free of the target and ligands which bind to the target through the first column at a linear velocity;
   (d) introducing an early portion of the eluant from the first column directly into a second column to determine the presence or absence of the first ligand and the second ligand;
   (e) introducing another sample of the solution to the first column;
   (f) passing a number of column volumes of a solvent free of the target and ligands which bind to the target through the first column at another linear velocity;
   (g) introducing an early portion of the eluant from the first column directly into the second column to determine the presence or absence of the first ligand and the second ligand; and
   (h) determining the relative binding affinities of at least the first ligand and the second ligand for the target based on the results of steps (d) and (g), where the presence of one of the first ligand and the second ligand at a decreased linear fluid velocity correlates to a higher relative binding affinity for that ligand to the target.

2. The method of claim 1 further comprising repeating steps (e)–(g) a desired number of times.

3. The method of claim 1 further comprising the step of identifying at least one of the first ligand or the second ligand.

4. The method of claim 3 wherein the step of identifying comprises using mass spectrometry.

5. The method of claim 1 wherein the second column is an affinity chromatography column.

6. The method of claim 1 wherein the second column is a ligand accumulator.

7. The method of claim 1 wherein the first ligand is selected from the group consisting of a protein, a peptide, a polysaccharide, and a polynucleotide.

8. The method of claim 3 further comprising the step of synthesizing an identified ligand.

9. A method of determining the presence of a ligand having a relatively high on-rate for a target in a solution of mixed ligands, the method comprising the steps of:

introducing a solution comprising a target and mixed ligands to a first column comprising a size exclusion medium, wherein at least a first ligand of the mixed ligands forms a first complex with the target; and eluting the first column with a solvent free of mixed ligands and the target at various linear fluid velocities to modulate the binding selectively of at least the first ligand to the target in preference to other mixed ligands, wherein at various linear fluid velocities early outputs comprising the first complex from the first column are indicative of the first ligand having a relatively high on-rate for the target compared to other mixed ligands in the solution.

10. The method of claim 9 comprising the additional steps of eluting an early portion of the output of the first column directly into a second column and eluting the second column to determine the presence of the first ligand.

11. The method of claim 10 wherein the second column is an affinity chromatography column.

12. The method of claim 10 wherein the second column is a ligand accumulator.

13. The method of claim 9 further comprising the step of identifying the first ligand.

14. The method of claim 13 wherein the step of identifying comprises using mass spectrometry.

15. The method of claim 10 further comprising the step of identifying the first ligand.

16. The method of claim 15 wherein the step of identifying comprises using mass spectrometry.

17. The method of claim 13 further comprising the step of synthesizing the first ligand.

18. The method of claim 9 wherein the first ligand is selected from the group consisting of a protein, a peptide, a polysaccharide, and a polynucleotide.

* * * * *